US010695200B2

(12) United States Patent
Wainwright et al.

(10) Patent No.: US 10,695,200 B2
(45) Date of Patent: Jun. 30, 2020

(54) ANTI-THROMBOGENIC MEDICAL DEVICES

(71) Applicant: Covidien LP, Mansfield, MA (US)

(72) Inventors: John Wainwright, Foothill Ranch, CA (US); Todd Mendelson, Mission Viejo, CA (US); Kurt Haggstrom, Mission Viejo, CA (US); Masoud Molaei, Westminster, CO (US); Victoria Schuman, Minneapolis, MN (US); Min-Shyan Sheu, Chelmsford, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/277,170

(22) Filed: Feb. 15, 2019

(65) Prior Publication Data
US 2019/0175373 A1 Jun. 13, 2019

Related U.S. Application Data

(63) Continuation of application No. 15/404,760, filed on Jan. 12, 2017, now Pat. No. 10,226,366, which is a (Continued)

(51) Int. Cl.
*A61F 2/90* (2013.01)
*A61F 2/07* (2013.01)
(Continued)

(52) U.S. Cl.
CPC .................. *A61F 2/90* (2013.01); *A61F 2/07* (2013.01); *B05D 1/18* (2013.01); *B05D 3/0272* (2013.01);
(Continued)

(58) Field of Classification Search
CPC .................. A61F 2/90; A61F 2002/823; A61F 2250/0067; A61F 2310/00359
See application file for complete search history.

(56) References Cited

U.S. PATENT DOCUMENTS 3,932,627 A 1/1976 Margraf
4,656,083 A 4/1987 Hoffman et al.
(Continued)

FOREIGN PATENT DOCUMENTS

CA 2683969 A1 10/2008
CN 1678366 A 10/2005
(Continued)

OTHER PUBLICATIONS

Bilgili et al., "Nano-milling of pigment agglomerates using a wet stirred media mill: Elucidation of the kinetics and breakage mechanisms", Chem. Eng. Sci. 2006; available online Jun. 21, 2005; (61(1)), pp. 149-157.
(Continued)

*Primary Examiner* — Brian A Dukert
(74) *Attorney, Agent, or Firm* — Shumaker & Sieffert, P.A.

(57) ABSTRACT

Medical devices that include a tubular member with a plurality of braided filaments, each filament crossing another of the filaments at a respective crossing point forming sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm, the pores have an average pore size that is less than or equal to about 500 microns when the tubular member is in an expanded state, the filaments possessing antithrombogenic surfaces to increase antithrombogenicity of the medical device with pores substantially free of webs formed by antithrombogenic material, such that fewer than 5% of the crossing points have webs formed by antithrombogenic material thereby permitting the pores to be substantially free of webs.

20 Claims, 21 Drawing Sheets

Related U.S. Application Data continuation of application No. 14/317,587, filed on Jun. 27, 2014, now Pat. No. 9,545,301, which is a continuation-in-part of application No. 13/844,577, filed on Mar. 15, 2013, now Pat. No. 9,320,592.

(51) Int. Cl.
  *B05D 1/18* (2006.01)
  *B05D 3/02* (2006.01)
  *B05D 3/04* (2006.01)
  *A61F 2/966* (2013.01)
  *A61F 2/82* (2013.01)

(52) U.S. Cl.
  CPC ............... *B05D 3/04* (2013.01); *A61F 2/966* (2013.01); *A61F 2002/072* (2013.01); *A61F 2002/823* (2013.01); *A61F 2002/9665* (2013.01); *A61F 2210/0076* (2013.01); *A61F 2230/0069* (2013.01); *A61F 2250/0023* (2013.01); *A61F 2250/0067* (2013.01); *A61F 2310/00389* (2013.01)

(56) References Cited

U.S. PATENT DOCUMENTS

| | | |
|---|---|---|
| 4,994,071 A | 2/1991 | MacGreqor |
| 5,013,306 A | 5/1991 | Solomon et al. |
| 5,019,096 A | 5/1991 | Fox, Jr. et al. |
| 5,217,492 A | 6/1993 | Guire et al. |
| 5,246,451 A | 9/1993 | Trescony et al. |
| 5,295,979 A | 3/1994 | DeLaurentis et al. |
| 5,360,440 A | 11/1994 | Andersen |
| 5,409,696 A | 4/1995 | Narayanan et al. |
| 5,419,760 A | 5/1995 | Narciso, Jr. |
| 5,449,382 A | 9/1995 | Dayton |
| 5,455,040 A | 10/1995 | Marchant |
| 5,464,650 A | 11/1995 | Berg et al. |
| 5,496,276 A | 3/1996 | Wanq et al. |
| 5,498,248 A | 3/1996 | Milder |
| 5,534,287 A | 7/1996 | Lukic |
| 5,567,495 A | 10/1996 | Modak et al. |
| 5,591,140 A | 1/1997 | Narayanan et al. |
| 5,591,225 A | 1/1997 | Okuda |
| 5,609,629 A | 3/1997 | Fearnot et al. |
| 5,616,338 A | 4/1997 | Fox, Jr. et al. |
| 5,618,316 A | 4/1997 | Hoffman et al. |
| 5,624,411 A | 4/1997 | Tuch |
| 5,624,449 A | 4/1997 | Pham et al. |
| 5,634,941 A | 6/1997 | Winston et al. |
| 5,643,580 A | 7/1997 | Subramaniam |
| 5,653,747 A | 8/1997 | Dereume |
| 5,665,103 A | 9/1997 | Lafontaine et al. |
| 5,667,523 A | 9/1997 | Bynon et al. |
| 5,674,241 A | 10/1997 | Bley et al. |
| 5,693,085 A | 12/1997 | Buirge et al. |
| 5,697,971 A | 12/1997 | Fischell et al. |
| 5,722,984 A | 3/1998 | Fischell et al. |
| 5,741,327 A | 4/1998 | Frantzen |
| 5,770,255 A | 6/1998 | Burrell et al. |
| 5,776,141 A | 7/1998 | Klein et al. |
| 5,824,045 A | 10/1998 | Ait |
| 5,824,049 A | 10/1998 | Ragheb et al. |
| 5,824,077 A | 10/1998 | Mayer |
| 5,837,313 A | 11/1998 | Ding et al. |
| 5,843,117 A | 12/1998 | Alt et al. |
| 5,866,113 A | 2/1999 | Hendriks et al. |
| 5,873,904 A | 2/1999 | Ragheb et al. |
| 5,888,577 A | 3/1999 | Griffin, III et al. |
| 5,897,911 A | 4/1999 | Loeffler |
| 5,902,283 A | 5/1999 | Darouiche et al. |
| 5,911,754 A | 6/1999 | Kanesaka et al. |
| 5,948,018 A | 9/1999 | Dereume et al. |
| 5,957,974 A | 9/1999 | Thompson et al. |
| 5,968,069 A | 10/1999 | Dusbabek et al. |
| 5,973,068 A | 10/1999 | Yamaya et al. |
| 5,976,169 A | 11/1999 | Lmran |
| 6,010,530 A | 1/2000 | Goicoechea |
| 6,019,789 A | 2/2000 | Dinh et al. |
| 6,022,374 A | 2/2000 | Lmran |
| 6,033,719 A | 3/2000 | Keogh |
| 6,048,910 A | 4/2000 | Furuya et al. |
| 6,051,020 A | 4/2000 | Goicoechea et al. |
| 6,066,167 A | 5/2000 | Lau et al. |
| 6,068,634 A | 5/2000 | Lorentzen et al. |
| 6,068,656 A | 5/2000 | Von Oepen |
| 6,106,548 A | 8/2000 | Roubin et al. |
| 6,156,373 A | 12/2000 | Zhong et al. |
| 6,159,531 A | 12/2000 | Dang et al. |
| 6,231,598 B1 | 5/2001 | Berry et al. |
| 6,268,348 B1 | 7/2001 | Bhatnagar |
| 6,306,165 B1 | 10/2001 | Patnaik et al. |
| 6,322,847 B1 | 11/2001 | Zhong et al. |
| 6,371,980 B1 | 4/2002 | Rudakov et al. |
| 6,461,735 B1 | 10/2002 | Furuya et al. |
| 6,652,574 B1 | 11/2003 | Jayaraman |
| 6,663,660 B2 | 12/2003 | Dusbabek et al. |
| 6,706,024 B2 | 3/2004 | Modak et al. |
| 6,979,348 B2 | 12/2005 | Sundar |
| 7,077,860 B2 | 7/2006 | Yan et al. |
| 7,198,675 B2 | 4/2007 | Fox et al. |
| 7,258,891 B2 | 8/2007 | Pacetti et al. |
| 7,297,159 B2 | 11/2007 | Hossainy et al. |
| RE40,722 E | 6/2009 | Chappa |
| 7,553,377 B1 | 6/2009 | Chen et al. |
| 7,563,277 B2 | 7/2009 | Case et al. |
| 7,563,324 B1 | 7/2009 | Chen et al. |
| 7,572,336 B2 | 8/2009 | Van Sciver et al. |
| 7,588,642 B1 | 9/2009 | Morris et al. |
| 7,604,700 B2 | 10/2009 | Fox et al. |
| 7,622,070 B2 | 11/2009 | Atladottir et al. |
| 7,632,307 B2 | 12/2009 | Pacetti et al. |
| 7,648,725 B2 | 1/2010 | Van Sciver et al. |
| 7,669,548 B2 | 3/2010 | Chappa |
| 7,704,544 B2 | 4/2010 | Pacetti et al. |
| 7,735,449 B1 | 6/2010 | Harold et al. |
| 7,771,743 B1 | 8/2010 | Luthra et al. |
| 7,820,284 B2 | 10/2010 | Terry et al. |
| 7,823,533 B2 | 11/2010 | Chen et al. |
| 7,833,544 B2 | 11/2010 | Lewis et al. |
| 7,939,095 B2 | 5/2011 | Zhao |
| 7,958,840 B2 | 6/2011 | Chappa |
| 7,959,942 B2 | 6/2011 | Cottone |
| 7,985,440 B2 | 7/2011 | Pacetti et al. |
| 7,985,441 B1 | 7/2011 | Tang et al. |
| 8,003,156 B2 | 8/2011 | Van Sciver |
| 8,069,814 B2 | 12/2011 | Guerriero et al. |
| 8,097,291 B2 | 1/2012 | Fredrickson et al. |
| 8,152,841 B2 | 4/2012 | Molaei et al. |
| 8,188,180 B2 | 5/2012 | Jonschker et al. |
| 8,197,879 B2 | 6/2012 | Fox et al. |
| 8,221,495 B2 | 7/2012 | Shrivastava et al. |
| 8,267,986 B2 | 9/2012 | Berez et al. |
| 8,273,101 B2 | 9/2012 | Garcia et al. |
| 8,282,979 B2 | 10/2012 | Larson et al. |
| 8,308,699 B2 | 11/2012 | Zhang et al. |
| 8,398,701 B2 | 3/2013 | Berez et al. |
| 8,409,269 B2 | 4/2013 | Berez et al. |
| 8,506,619 B2 * | 8/2013 | Ortiz ..................... A61F 2/90 |
| | | 623/1.16 |
| 8,591,566 B2 | 11/2013 | Newell et al. |
| 8,617,234 B2 | 12/2013 | Garcia et al. |
| 8,628,564 B2 | 1/2014 | Berez et al. |
| 8,668,919 B2 | 3/2014 | Ludwig et al. |
| 8,690,907 B1 | 4/2014 | Janardhan et al. |
| 8,778,008 B2 | 7/2014 | Amplatz et al. |
| 8,789,452 B1 | 7/2014 | Janardhan et al. |
| 8,801,777 B2 | 8/2014 | Elmaleh |
| 9,034,026 B2 | 5/2015 | Hannes et al. |
| 9,039,749 B2 | 5/2015 | Shrivastava et al. |
| 9,320,592 B2 | 4/2016 | Wainwright et al. |
| 9,545,301 B2 | 1/2017 | Wainwright et al. |
| 9,668,890 B2 | 6/2017 | Ma et al. |
| 10,226,366 B2 | 3/2019 | Wainwright et al. |

(56) References Cited

U.S. PATENT DOCUMENTS

| | | |
|---|---|---|
| 2001/0047202 A1 | 11/2001 | Slaikeu et al. |
| 2002/0058988 A1 | 5/2002 | Fischel et al. |
| 2002/0062145 A1 | 5/2002 | Rudakov et al. |
| 2003/0033007 A1 | 2/2003 | Sirhan et al. |
| 2003/0050691 A1 | 3/2003 | Shifrin et al. |
| 2004/0185081 A1 | 9/2004 | Verlee et al. |
| 2004/0236399 A1 | 11/2004 | Sundar |
| 2004/0249437 A1 | 12/2004 | Sundar |
| 2004/0254634 A1 | 12/2004 | Verlee et al. |
| 2005/0015142 A1 | 1/2005 | Austin et al. |
| 2005/0022915 A1 | 2/2005 | Bowen et al. |
| 2005/0060028 A1 | 3/2005 | Horres et al. |
| 2005/0107869 A1 | 5/2005 | Sirhan et al. |
| 2005/0137680 A1 | 6/2005 | Ortiz et al. |
| 2005/0158449 A1 | 7/2005 | Chappa |
| 2005/0175660 A1 | 8/2005 | Mollison et al. |
| 2005/0179011 A1 | 8/2005 | van Ooij et al. |
| 2005/0182474 A1 | 8/2005 | Jones et al. |
| 2006/0047336 A1 | 3/2006 | Gale et al. |
| 2006/0052757 A1 | 3/2006 | Fischer et al. |
| 2006/0088653 A1 | 4/2006 | Chappa |
| 2006/0177476 A1 | 8/2006 | Saffran |
| 2006/0206200 A1 | 9/2006 | Garcia et al. |
| 2007/0003753 A1 | 1/2007 | Asgari |
| 2007/0043428 A1 | 2/2007 | Jennings et al. |
| 2007/0050007 A1 | 3/2007 | Kondyurin et al. |
| 2007/0168019 A1 | 7/2007 | Amplatz et al. |
| 2007/0189915 A1 | 8/2007 | Shrivastava et al. |
| 2008/0033522 A1 | 2/2008 | Grewe et al. |
| 2008/0143659 A1 | 6/2008 | Ma |
| 2008/0145393 A1 | 6/2008 | Trollsas et al. |
| 2008/0188830 A1 | 8/2008 | Rosenblatt et al. |
| 2008/0206829 A1 | 8/2008 | Yu et al. |
| 2009/0011117 A1 | 1/2009 | Nunez et al. |
| 2009/0029961 A1 | 1/2009 | Modak et al. |
| 2009/0062899 A1 | 3/2009 | Dang et al. |
| 2009/0155335 A1 | 6/2009 | O'Shaughnessey et al. |
| 2009/0254174 A1 | 10/2009 | Case et al. |
| 2009/0312834 A1 | 12/2009 | Wood et al. |
| 2010/0131044 A1 | 5/2010 | Patel |
| 2010/0152834 A1 | 6/2010 | Hannes et al. |
| 2010/0179644 A1 | 7/2010 | Jennings et al. |
| 2010/0189808 A1 | 7/2010 | Gupta et al. |
| 2010/0191219 A1 | 7/2010 | Gupta et al. |
| 2010/0196434 A1 | 8/2010 | Gupta et al. |
| 2010/0198334 A1 | 8/2010 | Yodfat et al. |
| 2010/0215711 A1 | 8/2010 | Gupta et al. |
| 2010/0226955 A1 | 9/2010 | Ludwig et al. |
| 2010/0233288 A1 | 9/2010 | Gupta et al. |
| 2010/0234815 A1 | 9/2010 | Do et al. |
| 2010/0280587 A1 | 11/2010 | Ortiz et al. |
| 2011/0000658 A1 | 1/2011 | Tanaka et al. |
| 2011/0022149 A1 | 1/2011 | Cox et al. |
| 2011/0027757 A1 | 2/2011 | Kyomoto et al. |
| 2011/0039013 A1 | 2/2011 | Papp et al. |
| 2011/0054589 A1 | 3/2011 | Bashiri et al. |
| 2011/0152998 A1 | 6/2011 | Berez et al. |
| 2011/0208294 A1 | 8/2011 | Cottone |
| 2012/0021038 A1 | 1/2012 | Kloke et al. |
| 2012/0164458 A1 | 6/2012 | Biteau et al. |
| 2012/0197413 A1 | 8/2012 | Kyomoto et al. |
| 2012/0253369 A1 | 10/2012 | Morsi |
| 2012/0271396 A1 | 10/2012 | Zheng et al. |
| 2012/0283765 A1 | 11/2012 | Berez et al. |
| 2012/0301528 A1 | 11/2012 | Uhlmann et al. |
| 2012/0301530 A1 | 11/2012 | Uhlmann et al. |
| 2012/0303112 A1 | 11/2012 | Armstrong et al. |
| 2013/0226276 A1 | 8/2013 | Newell et al. |
| 2013/0226278 A1 | 8/2013 | Newell et al. |
| 2013/0231400 A1 | 9/2013 | Kim |
| 2013/0245745 A1 | 9/2013 | Vong et al. |
| 2013/0253572 A1 | 9/2013 | Molaei et al. |
| 2013/0304185 A1 | 11/2013 | Newell et al. |
| 2013/0315972 A1 | 11/2013 | Krasnow et al. |
| 2014/0277400 A1 | 9/2014 | Wainwright et al. |
| 2015/0066128 A1 | 3/2015 | Losordo et al. |
| 2015/0081003 A1 | 3/2015 | Wainwright et al. |
| 2015/0140344 A1 | 5/2015 | Ma et al. |
| 2015/0148882 A1 | 5/2015 | Ma et al. |
| 2016/0051263 A1 | 2/2016 | Morsi |
| 2017/0119557 A1 | 5/2017 | Wainwright et al. |
| 2017/0232156 A1 | 8/2017 | Ma et al. |
| 2019/0125555 A1 | 5/2019 | Ma et al. |

FOREIGN PATENT DOCUMENTS

| | | |
|---|---|---|
| CN | 1309353 C | 4/2007 |
| CN | 101212938 A | 7/2008 |
| CN | 101212990 A | 7/2008 |
| CN | 101234046 A | 8/2008 |
| CN | 101264346 A | 9/2008 |
| CN | 101677867 A | 3/2010 |
| CN | 102573701 A | 7/2012 |
| CN | 102579170 A | 7/2012 |
| DE | 19535068 A1 | 3/1997 |
| EP | 1000591 A2 | 5/2000 |
| EP | 1550477 A1 | 7/2005 |
| EP | 1883380 B1 | 3/2010 |
| JP | 2003290360 A | 10/2003 |
| JP | 2004526499 A | 9/2004 |
| JP | 2006051498 A | 2/2006 |
| JP | 2006521881 A | 9/2006 |
| JP | 2007236399 A | 9/2007 |
| JP | 2007536991 A | 12/2007 |
| JP | 2008518671 A | 6/2008 |
| JP | 2008173461 A | 7/2008 |
| JP | 2009502420 A | 1/2009 |
| JP | 2009240490 A | 10/2009 |
| JP | 2011525137 A | 9/2011 |
| JP | 2012523922 A | 10/2012 |
| JP | 2012527912 A | 11/2012 |
| KR | 10-2008-0067953 A | 7/2008 |
| WO | WO 9102537 A1 | 3/1991 |
| WO | WO 9810806 A1 | 3/1998 |
| WO | WO 9937242 A1 | 7/1999 |
| WO | WO 2000047134 A1 | 8/2000 |
| WO | WO 2000061034 A1 | 10/2000 |
| WO | WO 2002074194 A2 | 9/2002 |
| WO | WO 2003017852 A1 | 3/2003 |
| WO | WO 2004087017 A1 | 10/2004 |
| WO | WO 2005065579 A1 | 7/2005 |
| WO | WO 2005112570 A | 12/2005 |
| WO | WO 2006118863 A2 | 11/2006 |
| WO | WO 2007018980 A2 | 2/2007 |
| WO | WO 2008118132 A1 | 10/2008 |
| WO | WO 2009081870 A1 | 2/2009 |
| WO | WO 2010136075 A1 | 12/2010 |
| WO | WO 2013030819 A1 | 3/2013 |
| WO | WO 2014152608 A1 | 9/2014 |

OTHER PUBLICATIONS

BiodivYsio PMA POOOOII Summary of Safety and Effectiveness Data, Biocompalibles Cardiovascular Inc., Sep. 29, 2000, 26 pp.

Bridges et al., "Advances in drug eluting stents—focus on the Endeavor® zotarolimus stent," Medical Devices: Evidence and Research, Dec. 7, 2008, pp. 1-8.

Chen et al., "Surfaces having dual fibrinolytic and protein resistant properties by immobilization of lysine on polyurethane through a PEG spacer," Journal of Biomedical Materials Research Part A, Jul. 21, 2008, pp. 940-946.

Dow Corning, "A Guide to Silane Solutions," Dow Coming, 2005, accessed on Dec. 16, 2014; 30 pp.

Dumitriu, "Polymeric Biomalerials: Structure and Function," Table 25.6, CRC Press, Dec. 15, 2011, 1 pp.

Ehlers et al., "Theoretical Study on Mechanisms of the Epoxy-Amine Curing Reaction," Macromolecules, vol. 40, May 19, 2007, pp. 4370-4377.

Endeavor PMA P060033 Summary of Safety and Effectiveness Data, Medlronic Vascular, 2007, accessed on Dec. 16, 2014; 59 pp.

Examination Report from counterpart European Application No. 14719476.5, dated Mar. 9, 2017, 5 pp.

(56) References Cited

OTHER PUBLICATIONS

Examination Report from counterpart European Application No. 14719476.5, dated Oct. 20, 2016, 7 pp.
First Office Action and Search Report, and translation thereof, from counterpart Chinese Application No. 201480015573.X, dated May 5, 2016, 24 pp.
First Office Action and Search Report, and translation thereof, from counterpart Chinese Application No. 201710819642.8, dated Oct. 29, 2018, 21 pp.
Feng et al., "Atom-Transfer Radical Grafting Polymerization of 2-Methacryloyloxyethyl Phosphorylcholine from Silicon Wafer Surfaces," Journal of Polymer Science: Part A: Poymer Chemistry, vol. 42, Jan. 23, 2004, pp. 2931-2942.
Fu et al., "Surface Modification of Small Platinum Nanoclusters with Alkylamine and Alkylthiol: An KPS Study on the Influence of Organic Ligands on the PI 4f Binding Energies of Small Platinum Nanoclusters," Journal of Colloid and Interface Science, Nov. 2001, vol. 243, Issue 2, pp. 326-330.
Gelest, Inc., "Silane Coupling Agents: Connecting Across Boundaries," version 2, 2006, accessed on Dec. 16, 2014; 59 pp.
"A Guide to Silane Solutions from Dow Corning," Dow Corning Corporation, 2005, 32 pp. (Applicant points out that, in accordance with MPEP 609.04(a), the 2005 year of publication is sufficiently earlier than the effective U.S. filing date and any foreign priority date of Nov. 22, 2013 so that the particular month of publication is not in issue.)
Intent to Grant from counterpart European Patent Application No. 14719476.5, dated Nov. 14, 2017, 118 pp.
International Preliminary Report on Patentability from International Application No. PCT/US2014/027526, dated Sep. 15, 2015, 7 pp.
International Preliminary Report on Patentability from International Application No. PCT/US2015/037886, dated Apr. 13, 2017, 8 pp.
International Search Report and Written Opinion from International Application No. PCT/US2014/027526, dated Jul. 28, 2014, 10 pp.
Kang et al., "Fabrication of biofunctional stents with endothelial progenitor cell specificity for vascular re-endothelialization," Colloids and Surfaces B: Biointerfaces, vol. 102, Sep. 17, 2012, pp. 744-751.
Lee et al., "Covalent incorporation of starch derivative into waterborne polyurethane for biodegradability," Carbohydrate Polymers, vol. 87, Oct. 6, 2011, pp. 1803-1809.
Lewis et al., "Poly(2-methacryloyloxyethyl phosphorylcholine) for Protein Conjugation," Bioconjugate Chemistry, vol. 19, Sep. 19, 2008, pp. 2144-2155.
Lin et al., "Surface characterization and platelet adhesion studies on polyurethane surface immobilized with C60," Biomaterials, vol. 20, Mar. 31, 1999, pp. 1613-1620.
Love et al., "Self-Assembled Monolayers of Thiolates on Metals as a Form of Nanotechnology," Chem, Rev, vol. 105, Mar. 25, 2005, pp. 1103-1169.
Luzinov, et al., "Epoxy-Terminated Self-Assembled Monolayers: Molecular Glues for Polymer La ers," Lan muir, 2000, received Apr. 26, 1999; vol. 16, pp. 504-516.
McAuliffe et al., "Immediate and Midterm Results following Treatment of Recently Ruptured Intracranial Aneurysms with the Pipeline Embolization Device," AJNR, Am J. Neuroradiol, vol. 33, Mar. 2012, pp. 487-493.
Notice of Allowance, and translation thereof, from counterpart Chinese Application No. 201480015573.X, dated Jun. 29, 2017, 3 pp.
Notice of Final Rejection, and translation thereof, from counterpart Japanese Application No. 2016-502472, dated Jan. 17, 2017, 7 pp.
Notice of Final Rejection, and translation thereof, from counterpart Korean Application No. 10-2015-7024827, dated Apr. 3, 2017, 5 pp.
Notice of Pre-Appeal Examination Report, and translation thereof, from counterpart Japanese Application No. 2016-502472, dated Jul. 14, 2017, 7 pp.
Notice of Preliminary Rejection, and translation thereof, from counterpart Korean Application No. 10-2015-7024827, dated May 23, 2016, 6 pp.
Notice of Preliminary Rejection, and translation thereof, from counterpart Korean Application No. 10-2015-7024827, dated Jan. 2, 2017, 10 pp.
Notice of Reasons for Rejection, and translation thereof, from counterpart Japanese Application No. 2016-502472, dated Apr. 25, 2016, 13 pp.
Notice of Reasons for Rejection, and translation thereof, from counterpart Japanese Application No. 2017098118, dated Mar. 29, 2018, 10 pp.
The Notification of Reason for Rejection, and translation thereof, from counterpart Japanese Application No. 2016-502472, dated Sep. 26, 2018, 13 pp.
"Product description for Lipidure-PC (MPC monomer) retrieved on Sep. 10, 2015, from http://nofamerica. net/store/index. ph p?dispatch=categories.view&category_id= 145".
"Product description for Lipidure-CM (MPC polymer) retrieved on Apr. 9, 2013, from http://nofamerica. net/store/index. ph p?dispatch=categories. view&category_id= 146".
"Product description for Reactive MPC Polymers retrieved on Sep. 10, 2015, from http://nofamerica. net/store/index. ph p?dispatch=categories. view&category_id=212".
Prosecution History from U.S. Appl. No. 13/844,577, dated Jul. 1, 2014 through Jan. 25, 2016, 67 pp.
Prosecution History from U.S. Appl. No. 14/317,587, dated Dec. 23, 2015 through Dec. 8, 2016, 55 pp.
Prosecution History from U.S. Appl. No. 15/404,760, dated Jan. 13, 2017 through Dec. 19, 2018, 41 pp.
Ren et al., "Hemocompatibility Evaluation of Polyurethane Film with Surface-Grafted Poly (ethylene glycol) and Carboxymethyl-Chitosan," Journal of Applied Polymer Science, May 4, 2012, pp. 308-315.
Report of Reconsideration by Examiner before Appeal, and machine translation thereof, from counterpart Japanese No. 2016-502472, dated Jul. 14, 2017, 6 pp.
Sanchis et al., "Surface Modification of a Polyurethane Film by Low Pressure Glow Discharge Oxygen Plasma Treatment," Journal of Applied Polymer Science, vol. 105, Apr. 9, 2007, pp. 1077-1085.
The Second Notification of Reason for Rejection, and translation thereof, from counterpart Korean Application No. 10-2015-7024827, dated Jun. 7, 2017, 5 pp.
Second Office Action, and machine translation thereof, from counterpart Chinese Application No. 201480015573.X, dated Mar. 1, 2017, 7 pp.
Sidouni et al., "Surface properties of a specifically modified high-grade medical polyurethane," Surface Science, vol. 491, Apr. 26, 2001, pp. 355-369.
"Summary of Safety and Effectiveness Data," Oct. 10, 2007, 59 pp.
Troughton, et al., "Monolayer Films Prepared by the Spontaneous Self-Assembly of Symmetrical and Unsymmetrical Dialkyl Sulfides from Solution onto Gold Substrates: Structure, Properties, and Reactivity of Constituent Functional Groups," Langmuir, 1988, vol. 4, pp. 365-385.
Tsukruk et al., "Sticky Molecular Surfaces: Epoxysilane Self-Assembled Monolayers," Langmuir, vol. 15, Apr. 1, 1999, pp. 3029-3032.
Yakai et al., "Surface Modification of Polycarbonate Urethane by Covalent Linkage of Heparin with a PEG Spacer," Tianjin University and Springer-Verlag Berlin Heidelberg, vol. 19, Feb. 9, 2013, pp. 58-65.
Zhang et al., "Superlow Fouling Sulfobetaine and Carboxybetaine Polymers on Glass Slides," Langmuir, Vol: 22, Oct. 28, 2006, pp. 10072-10077.
Second Office Action and Search Report, and translation thereof, from counterpart Chinese Application No. 201710819642.8, dated Jul. 12, 2019, 11 pp.
U.S. Appl. No. 16/586,639, filed Sep. 27, 2019, by Ma et al.
Examination Report, and translation thereof, from counterpart Indian Application No. 8250/DELNP/2015, dated Dec. 24, 2019, 6 pp.
Notice of Preliminary Rejection, and translation thereof, from counterpart Korean Application No. 10-2017-7018628, dated Dec. 9, 2019, 6 pp.

(56) References Cited

OTHER PUBLICATIONS

Office Action and Search Report, and informal translation thereof, from counterpart Brazilian Application No. BR112015020893-2, dated Jan. 17, 2020, 5 pp.

* cited by examiner

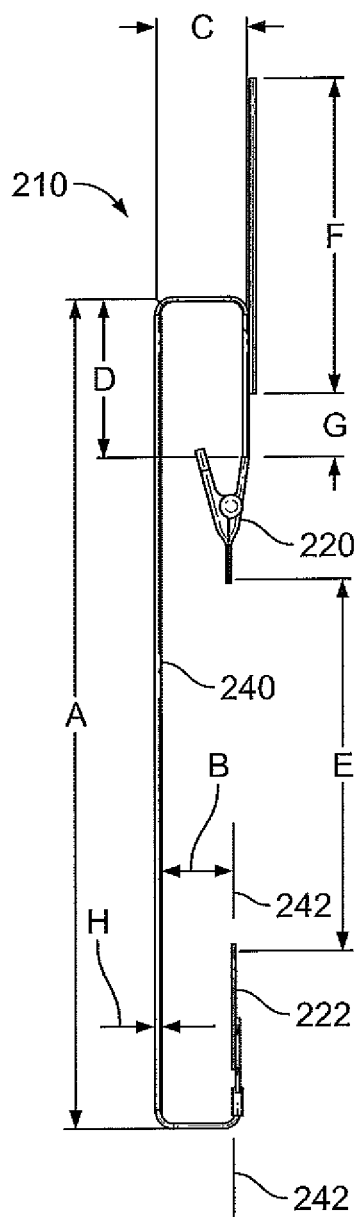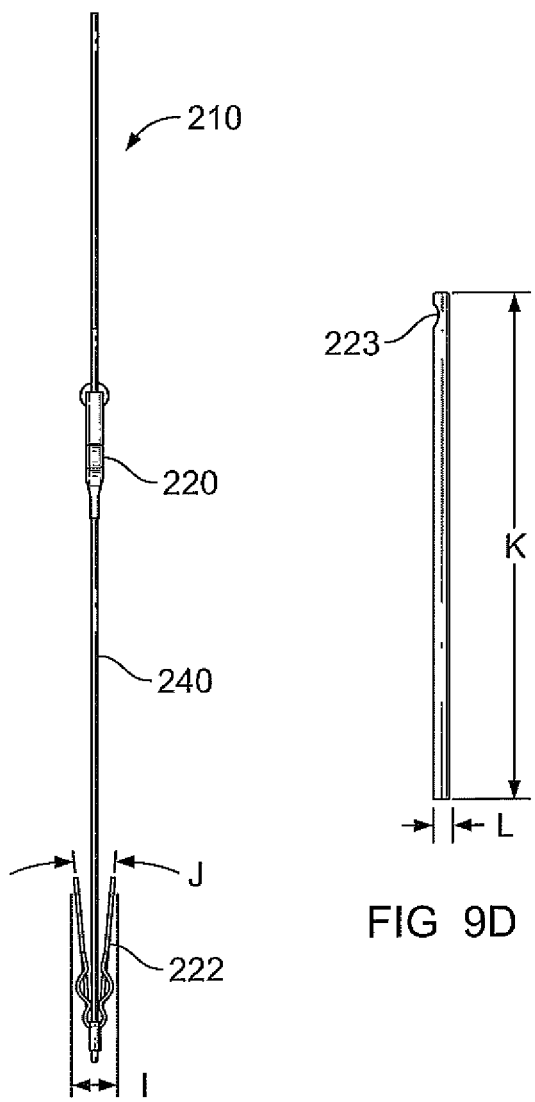
FIG. 9B  FIG. 9C  FIG 9D

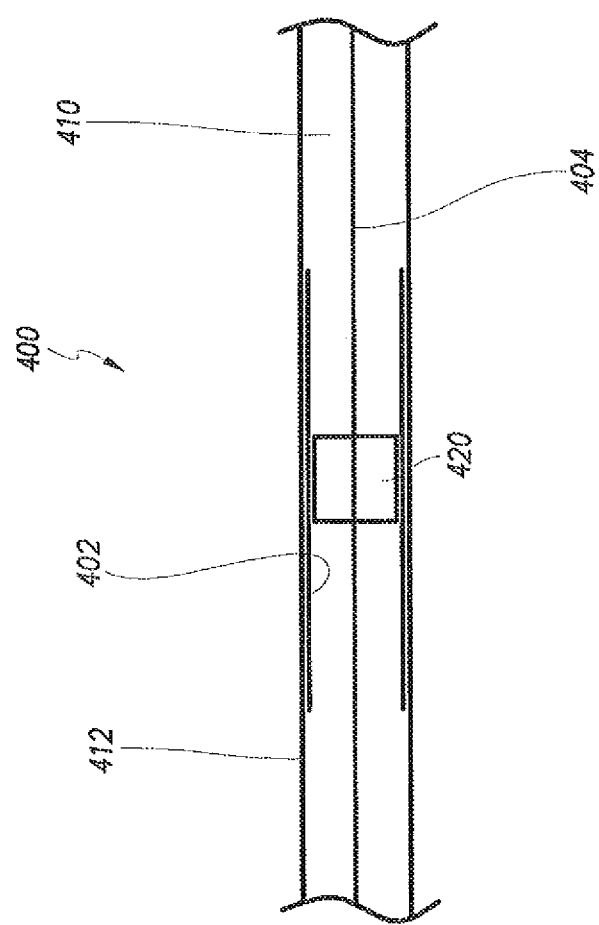

ANTI-THROMBOGENIC MEDICAL DEVICES

RELATED APPLICATIONS

This application is a continuation of U.S. patent application Ser. No. 15/404,760, filed on Jan. 12, 2017, which is a continuation of U.S. patent application Ser. No. 14/317,587, filed on Jun. 27, 2014, now patented as U.S. Pat. No. 9,545,301, which is a continuation-in-part of U.S. patent application Ser. No. 13/844,577, filed Mar. 15, 2013, now patented as U.S. Pat. No. 9,320,592, the entire contents of each of which are incorporated by reference herein and made a part of this specification.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such exclusion is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide therapy or support against blockage of the vessel. Methods for delivering these intravascular stents are also well known.

Various other implantable devices are used in surgical procedures. Often, these stents and other devices are coated with a coating material in order to achieve a desired therapeutic or other effect.

SUMMARY

In accordance with some embodiments disclosed herein, a heat-treated device (e.g., stent) is provided that comprises an even coating that is substantially free of imperfections, such as lumps, fibers, webs, and/or other obstructions in the pores of the device. Such a device can be braided and/or have a flow diverting section.

Aspects of some embodiments disclosed herein recognize the existence of significant challenges in manufacturing a flow diverting device, such as a stent, that has a coating evenly applied over its surface. Hitherto, no process or device known to the Applicants has been developed that provides a device, such as a braided stent, with a coating that is evenly distributed over its surface, e.g., a coating that is devoid of imperfections, such as lumps, webs, fibers, or other obstructions in the pores of the stent.

Some embodiments disclosed herein provide a device with at least one flow diverting section that is coated and substantially free of webbing or that has a substantially uniform coating. Some embodiments relate to coating processes by which a device (e.g., a braided stent) can receive an even, generally imperfection-free coating. Additionally, some embodiments relate to methods of treatment using such coated devices (e.g., braided stents). Furthermore, some embodiments relate to one or more of the various advantageous features of the coated devices (e.g., braided stents).

For example, in some embodiments a medical device is provided for treating an aneurysm. The device can comprise a tubular body comprising a plurality of braided filaments and configured to be implanted in a blood vessel. The body can be expandable to an expanded state for treatment of the aneurysm. The body can have a first section for spanning the neck of the aneurysm and a plurality of pores located between the filaments. The pores in the first section can have a first average pore size of less than about 500 microns when the body is in the expanded state. The first section can have a substantially complete coating, comprising a coating material, over the filaments. Further, the first section can be substantially free of webs formed between the braided filaments by the coating material.

The first section can comprise a length less than an entire length of the tube. The coating material on the first section can be generally uniform over the device or filaments. The coating can comprise an antithrombogenic material.

The medical device can further comprise a second section having a plurality of pores having a second average pore size greater than the first average pore size.

Further, some embodiments can provide a delivery system for treating an aneurysm. The system can comprise a microcatheter configured to be implanted into a blood vessel, a core assembly, extending within the microcatheter, having a distal segment, and the device extending along the core assembly distal segment.

Furthermore, the medical device can comprise a tubular member having a sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm. The device can also have an anti-thrombogenic coating distributed over the tubular member such that the pores are substantially free of webs formed by the coating.

The pores can have an average pore size that is the average size of the pores in the first section without the coating material. The coating can be substantially complete over the device or tubular member. The coating can be generally uniform over the device or tubular member. The device or tubular member can comprise a plurality of braided filaments. The device or tubular member can be substantially free of webs formed between the braided filaments by the coating. The flow diverting pores can extend over less than a longitudinal length that is less than a longitudinal length of the device or tubular member.

The device can comprise a tubular member comprising a plurality of filaments that are braided together to form pores therebetween. The tubular member can have a flow diverting section configured to span the neck of the aneurysm. The device can also have a coating distributed over the flow diverting section. The coating is distributed completely over the flow diverting section substantially free of imperfections such that coated first and second longitudinal segments of the flow diverting section of approximately the same longitudinal lengths have approximately equal weights.

A medical device for treating an aneurysm can also be provided that comprises a tubular member comprising a plurality of filaments, formed from a first material, that are braided together to form pores therebetween. The device can also comprise a coating material distributed over the filaments to form a coated flow diverting section that is substantially free of webs formed between the filaments by the coating material. The coating material can be distributed such that the device is significantly less thrombogenic than an uncoated device formed from the first material.

The coating material can be one or more of a variety of anti-thrombogenic materials or platelet aggregation inhibitors, or anti-thrombogenic polymers or monomers. Suitable coating materials include 2-Methacryloyloxyethyl phosphorylcholine (MPC, available as LIPIDURE™ from NOF Corporation of Tokyo, Japan). A suitable form of MPC is LIPIDURE™-CM2056, or 2-Methacryloyloxyethyl phosphorylcholine-poly(n-butyl methacrylate). Additional suitable coating materials include PARYLENE C™, or PARYLENE HT™, both available from Specialty Coating Systems of Indianapolis, Ind.; BAYMEDIX™ available from Bayer AG of Leverkusen, Germany; BIOCOAT™ hyaluronic acid available from BioCoat, Inc. of Horsham, Pa.; or polyethylene oxide. Other coating materials include heparin, heparin-like materials or derivatives, hirudin, H-Heparin, HSI-Heparin, albumin, phospholipids, streptokinase, tissue plasminogen activator (TPA), urokinase, hyaluronic acid, chitosan, methyl cellulose, poly(ethylene oxide), poly(vinyl pyrrolidone), endothelial cell growth factor, epithelial growth factor, osteoblast growth factor, fibroblast growth factor, platelet derived growth factor or angiogenic growth factor.

In some embodiments, the pores can have an average pore size that is less than or equal to about 500 microns. The pores can have an average pore size that is less than or equal to about 320 microns. The pores can have an average pore size that is from about 50 microns to about 320 microns. The pores can have a pore size that is generally constant. The pores can have an average pore size that is measured using an inscribed circle diameter.

Some embodiments of processes disclosed herein comprise mounting or maintaining a braided, flow diverting device (e.g., stent) in a longitudinally stretched configuration during the coating process in order to prevent coating imperfections, such as webbing. The longitudinally stretched configuration can enable individual filaments of the braided device to overlap each other at angles of between about 75 degrees and about 105 degrees with respect to each other. The longitudinally stretched configuration can enable individual filaments of the braided device to overlap each other at angles of between about 80 degrees and about 100 degrees with respect to each other. Further, the longitudinally stretched configuration can enable individual filaments of the braided device to overlap each other at angles of between about 85 degrees and about 95 degrees with respect to each other. Furthermore, the longitudinally stretched configuration can enable individual filaments of the braided device to overlap each other approximately perpendicularly or at a generally right angles with respect to each other. In some embodiments, therefore, the longitudinally stretched configuration can orient the individual filaments to create a pattern of quadrilaterals, such as squares, rectangles, parallelograms, rhombuses, trapezoids, etc.

Further, some embodiments of processes disclosed herein comprise dipping a longitudinally stretched braided device (e.g., stent) in a coating solution and thereafter air knifing the dipped device. The process of air knifing can comprise applying at least one powerful jet of air to remove or blow off any excess solution from the device. The air jet(s) of the air knife(s) can be applied in a direction that is generally transverse, such as orthogonal, relative to the longitudinal axis of the device. The air knife can be stationary while the device is moved or it can move along and/or about the device as the device remains stationary.

In some embodiments, the longitudinally stretched braided device (e.g., stent) can alternatively be coated with a coating solution using a spraying operation. In some embodiments, while the device is being coated, the device can be rotated about its central longitudinal axis to ensure even application of the air jet or sprayed coating.

For example, a method of coating a stent is provided wherein the method comprises: attaching first and second ends of the stent with upper and lower connectors of a holder device, the stent comprising a flow diverting section; dipping the stent into a coating material to coat a first section of the stent; and removing excess coating material from the stent such that the stent is free of webs formed by the coating material.

The method can be performed such that the flow diverting section comprises a plurality of pores having an average pore size that is less than or equal to about 500 microns. Further, the average pore size can be less than or equal to about 320 microns. The average pore size can be from about 50 microns to about 320 microns.

The method can be performed such that dipping the stent into the coating material comprises dipping less than an entire length of the stent into the coating material to maintain an open air pocket adjacent to the stent first end. Further, attaching the first and second ends of the stent can comprise attaching the stent to the holder device such that the stent is held between the upper and lower connectors in a radially collapsed, longitudinally elongated state. The stent can comprise a plurality of braided filaments, and the stent filaments can cross each other at substantially right angles when the stent is held in the elongated state. Further, the elongated state can be achieved when the stent filaments cross each other at angles in an angular range from about 80° to about 110°. In addition, the stent can comprise a plurality of braided filaments, and the coating material on the stent can be substantially free of webs such that the coating material does not bridge between adjacent filaments.

Additionally, some embodiments of the coating (e.g., dipping, spraying, etc.) processes disclosed herein can be performed using a cantilevered fixture. One of the inventive realizations of some embodiments is that a cantilevered fixture, which can be suitable for use in, for example, a dipping process, can also be designed to be suitable for use in air knifing processes, when necessary. In order to be suitable for air knifing processes, however, the cantilevered fixture can beneficially be configured to resist deflection, such as the "pendulum effect" that occurs when an air jet is applied to the mounted device, and the device and the fixture begin to move back and forth harmonically, off-axis. Further, the cantilevered fixture can also beneficially be configured to mount the device thereto without passing through a lumen of the device or otherwise interfering with air flow from the air knife. Furthermore, the cantilevered fixture can also beneficially avoid contact with the device in order to prevent wicking or removing solution from the surface of the device.

Accordingly, in some embodiments, the cantilevered fixture can be both rigid and lightweight. For example, a lower (free) end of the cantilevered fixture can be lighter weight than an upper (cantilevered) end of the cantilevered fixture.

Further, in some embodiments, the cantilevered fixture can comprise first and second ends that engage with corresponding ends of the device (e.g., stent) and a fixture body that extends between the first and second ends and outside of a device lumen when the device is mounted to the fixture. The first end can comprise one or more clips or protrusions that engage a first end of the device, such as by pinching, grasping, friction, and/or hook and loop, or other mechanical fastening means. The second end can comprise one or more clips or protrusions that engage an opposing end of the device, such as by pinching, grasping, friction, and/or a hook and loop or other mechanical fastening means. The first and second ends can be upper or lower ends of the cantilevered fixture. The first and second ends can be spaced apart sufficiently to maintain the device in a longitudinally stretched configuration when mounted on the cantilevered fixture.

In accordance with some embodiments, a method of coating a stent is provided in which the method comprises: attaching a first end of the stent with an upper connector of a holder device, the stent comprising a plurality of braided filaments; attaching a second end of the stent with a lower connector of the holder device such that the stent is held between the upper and lower connectors in a radially collapsed, longitudinally elongated state, the stent filaments crossing each other at substantially right angles when the stent is held in the elongated state; while maintaining the stent in the elongated state, dipping the stent into a coating material to coat a first section of the stent; and removing excess coating material from the stent.

The elongated state can be achieved when the stent filaments cross each other at angles ranging from about 80° to about 110°. Further, the elongated state can be achieved when the stent filaments cross each other at angles in a range from about 85° to about 95°.

The method can be performed such that removing excess coating material comprises applying a stream of gas to the stent filaments. The stream of gas can be of a sufficient strength to remove excess coating material from the stent. Further, removing excess coating material can comprise rotating the stent and holder device while applying a stream of gas to impinge upon an outer surface of the stent. Furthermore, the method can comprise drying the coating material applied to the stent. For example, the drying can comprise drying the stent in an oven at between from about 50° to about 80° for between from about 5 minutes to about 1 hour, and in some embodiments, at about 60° for about 15 minutes.

The method can be performed such that dipping the stent into the coating material comprises dipping less than an entire length of the stent into the coating material to maintain an open air pocket adjacent to the stent first end. Further, the holder device upper and lower connectors can be interconnected such that the holder device is in a cantilevered configuration during the dipping and removing steps.

In some embodiments, a method of coating a stent can be provided that comprises: attaching a first end of the stent with an upper connector of a holder device, the stent comprising a plurality of braided filaments and a plurality of pores located between the filaments; attaching a second end of the stent with a lower connector of the holder device such that the stent is held between the upper and lower connectors in a radially collapsed, longitudinally elongated state in which the filaments are oriented to substantially maximize an average inscribed area of the pores; while maintaining the stent in the elongated state, dipping the stent into a coating material to coat a first section of the stent; and removing excess coating material from the stent.

The method can be performed such that the maximum average inscribed area of the pores is achieved when the filaments cross each other at substantially right angles. The maximum average inscribed area of the pores can be achieved when the pores are substantially square. The maximum average inscribed area of the pores can be achieved when the filaments cross each other at angles in a range from about 80° to about 110°. Further, the maximum average inscribed area of the pores can be achieved when the filaments cross each other at angles in a range from about 85° to about 95°.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A medical device for treating an aneurysm, comprising:
a tubular body configured to be implanted in a blood vessel and comprising a plurality of braided filaments, the body being expandable to an expanded state for treatment of the aneurysm, the body having a first section for spanning the neck of the aneurysm and a plurality of pores located between the filaments, the pores in the first section having a first average pore size of less than about 500 microns when the body is in the expanded state;
the first section having a substantially complete coating, comprising a coating material, over the filaments;
wherein the first section is substantially free of webs formed between the braided filaments by the coating material.

Clause 2. The medical device of Clause 1, wherein the first average pore size is less than or equal to about 320 microns.

Clause 3. The medical device of Clause 2, wherein the first average pore size is from about 50 microns to about 320 microns.

Clause 4. The medical device of Clause 1, wherein the first average pore size is measured using an inscribed circle diameter.

Clause 5. The medical device of Clause 1, wherein the first average pore size is the average size of the pores in the first section without the coating material.

Clause 6. The medical device as in Clause 1, wherein the first section comprises less than an entire length of the tube.

Clause 7. The medical device as in Clause 1, wherein the coating material on the first section is generally uniform over the filaments.

Clause 8. The medical device as in Clause 1, wherein the coating comprises an antithrombogenic material.

Clause 9. The medical device as in Clause 8, wherein the coating comprises an antithrombogenic polymer.

Clause 10. The medical device as in Clause 8, wherein the coating comprises MPC.

Clause 11. The medical device as in Clause 1, further comprising a second section having a plurality of pores having a second average pore size greater than the first average pore size.

Clause 12. The medical device as in Clause 1, wherein the first section comprises a circumferential portion of the device that is at least 5 mm in length.

Clause 13. A delivery system for treating an aneurysm, the system comprising:

a microcatheter configured to be implanted into a blood vessel;

a core assembly, extending within the microcatheter, having a distal segment; and the device of Clause 1 extending along the core assembly distal segment.

Clause 14. The medical device as in Clause 1, wherein the filaments comprise heat-treated metallic filaments.

Clause 15. The medical device as in Clause 1, wherein the tubular body comprises a heat-set metallic braid.

Clause 16. The medical device as in Clause 1, wherein the tubular body is self-expanding.

Clause 17. The medical device as in Clause 1, wherein the device is less thrombogenic than an identical, uncoated device.

Clause 18. The medical device as in Clause 17, wherein the device exhibits an elapsed time before peak thrombin formation that is at least 1.5 times the elapsed time of the identical, uncoated device.

Clause 19. The medical device as in Clause 1, wherein the tubular body has an open proximal end, an open distal end, and forms a lumen extending from the proximal end to the distal end.

Clause 20. A medical device for treating an aneurysm, comprising:

a tubular member having a sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm; and an anti-thrombogenic coating distributed over the tubular member such that the pores are substantially free of webs formed by the coating.

Clause 21. The medical device of Clause 20, wherein the pores have an average pore size that is less than or equal to about 500 microns.

Clause 22. The medical device of Clause 21, wherein the pores have an average pore size that is less than or equal to about 320 microns.

Clause 23. The medical device of Clause 22, wherein the pores have an average pore size that is from about 50 microns to about 320 microns.

Clause 24. The medical device of Clause 20, wherein the pores have an average pore size that is measured using an inscribed circle diameter.

Clause 25. The medical device of Clause 20, wherein the pores have an average pore size that is the average size of the pores in the first section without the coating material.

Clause 26. The device of Clause 20, wherein the coating is substantially complete over the tubular member.

Clause 27. The device of Clause 26, wherein the coating is generally uniform over the tubular member.

Clause 28. The device of Clause 20, wherein the coating is substantially complete over at least a circumferential section of the device that is 5 mm or more in length.

Clause 29. The medical device of Clause 20, wherein the tubular member comprises a plurality of braided filaments.

Clause 30. The medical device as in Clause 29, wherein the filaments comprise heat-treated metallic filaments.

Clause 31. The medical device as in Clause 29, wherein the tubular member comprises a heat-set metallic braid.

Clause 32. The medical device as in Clause 29, wherein the tubular member is substantially free of webs formed between the braided filaments by the coating.

Clause 33. The medical device as in Clause 20, wherein the tubular member is self-expanding.

Clause 34. The medical device of Clause 20, wherein the flow diverting pores extend over less than a longitudinal length that is less than a longitudinal length of the tubular member.

Clause 35. The medical device as in Clause 20, wherein the device is less thrombogenic than an identical, uncoated device.

Clause 36. The medical device as in Clause 35, wherein the device exhibits an elapsed time before peak thrombin formation that is at least 1.5 times the elapsed time of the identical, uncoated device.

Clause 37. The medical device as in Clause 20, wherein the tubular body has an open proximal end, an open distal end, and forms a lumen extending from the proximal end to the distal end.

Clause 38. A medical device for treating an aneurysm, comprising:

a tubular member comprising a plurality of filaments that are braided together to form pores therebetween, the tubular member having a flow diverting section configured to span the neck of the aneurysm; and a coating distributed over the flow diverting section;

wherein the coating is distributed completely over the flow diverting section substantially free of imperfections such that coated first and second longitudinal segments of the flow diverting section of approximately the same longitudinal lengths have approximately equal weights.

Clause 39. The medical device of Clause 38, wherein the pores in the flow diverting section have an average pore size that is less than or equal to about 500 microns.

Clause 40. The medical device of Clause 39, wherein the average pore size is less than or equal to about 320 microns.

Clause 41. The medical device of Clause 40, wherein the average pore size is from about 50 microns to about 320 microns.

Clause 42. The medical device of Clause 38, wherein the pores in the flow diverting section have a pore size that is generally constant.

Clause 43. The medical device of Clause 38, wherein the coating is generally uniform over the flow diverting section.

Clause 44. The medical device as in Clause 38, wherein the filaments comprise heat-treated metallic filaments.

Clause 45. The medical device as in Clause 38, wherein the tubular member comprises a heat-set metallic braid.

Clause 46. A method of coating a stent, the method comprising:

attaching first and second ends of the stent with upper and lower connectors of a holder device, the stent comprising a flow diverting section;

dipping the stent into a coating material to coat a first section of the stent; and removing excess coating material from the stent such that the stent is free of webs formed by the coating material.

Clause 47. The method of Clause 46, wherein the flow diverting section comprises a plurality of pores having an average pore size that is less than or equal to about 500 microns.

Clause 48. The method of Clause 47, wherein the average pore size is less than or equal to about 320 microns.

Clause 49. The method of Clause 48, wherein the average pore size is from about 50 microns to about 320 microns.

Clause 50. The method of Clause 46, wherein dipping the stent into the coating material comprises dipping less than an entire length of the stent into the coating material to maintain an open air pocket adjacent to the stent first end.

Clause 51. The method of Clause 46, wherein attaching the first and second ends of the stent comprises attaching the stent to the holder device such that the stent is held between the upper and lower connectors in a radially collapsed, longitudinally elongated state.

Clause 52. The method of Clause 51, wherein the stent comprises a plurality of braided filaments, and wherein the stent filaments cross each other at substantially right angles when the stent is held in the elongated state.

Clause 53. The method of Clause 52, wherein the elongated state is achieved when the stent filaments cross each other at angles in an angular range from about 80° to about 110°.

Clause 54. The method of Clause 46, wherein the stent comprises a plurality of braided filaments, and the coating material on the stent is substantially free of webs such that the coating material does not bridge between adjacent filaments.

Clause 55. A method of coating a stent, the method comprising:
attaching a first end of the stent with an upper connector of a holder device, the stent comprising a plurality of braided filaments;
attaching a second end of the stent with a lower connector of the holder device such that the stent is held between the upper and lower connectors in a radially collapsed, longitudinally elongated state, the stent filaments crossing each other at substantially right angles when the stent is held in the elongated state;
while maintaining the stent in the elongated state, dipping the stent into a coating material to coat a first section of the stent; and
removing excess coating material from the stent.

Clause 56. The method of Clause 55, wherein the elongated state is achieved when the stent filaments cross each other at angles in an angular range from about 80° to about 110°.

Clause 57. The method of Clause 56, wherein the elongated state is achieved when the stent filaments cross each other at angles in an angular range from about 85° to about 95°.

Clause 58. The method of Clause 55, wherein removing excess coating material comprises applying a stream of gas to the stent filaments, the stream of gas being of a sufficient strength to remove excess coating material from the stent.

Clause 59. The method of Clause 55, wherein removing excess coating material comprises rotating the stent and holder device while applying a stream of gas to impinge upon an outer surface of the stent.

Clause 60. The method of Clause 55, further comprising drying the coating material applied to the stent.

Clause 61. The method of Clause 55, wherein dipping the stent into the coating material comprises dipping less than an entire length of the stent into the coating material to maintain an open air pocket adjacent to the stent first end.

Clause 62. The method of Clause 55, wherein the holder device upper and lower connectors are interconnected such that the holder device is in a cantilevered configuration during the dipping and removing steps.

Clause 63. A method of coating a stent, the method comprising:
attaching a first end of the stent with an upper connector of a holder device, the stent comprising a plurality of braided filaments and a plurality of pores located between the filaments;
attaching a second end of the stent with a lower connector of the holder device such that the stent is held between the upper and lower connectors in a radially collapsed, longitudinally elongated state in which the filaments are oriented to substantially maximize an average inscribed area of the pores;
while maintaining the stent in the elongated state, dipping the stent into a coating material to coat a first section of the stent; and
removing excess coating material from the stent.

Clause 64. The method of Clause 63, wherein the maximum average inscribed area of the pores is achieved when the filaments cross each other at substantially right angles.

Clause 65. The method of Clause 63, wherein the maximum average inscribed area of the pores is achieved when the pores are substantially square.

Clause 66. The method of Clause 63, wherein the maximum average inscribed area of the pores is achieved when the filaments cross each other at angles in an angular range from about 80° to about 110°.

Clause 67. The method of Clause 66, wherein the maximum average inscribed area of the pores is achieved when the filaments cross each other at angles in an angular range from about 85° to about 95°.

Clause 68. A medical device for treating an aneurysm, the device comprising:
a tubular member comprising a plurality of filaments, formed from a first material, that are braided together to form pores therebetween; and
a coating material distributed over the filaments to form a coated flow diverting section that is substantially free of webs formed between the filaments by the coating material, the coating material distributed such that the device is less thrombogenic than a similar but uncoated device.

Clause 69. The device of Clause 68, wherein the coating material comprises an antithrombogenic polymer.

Clause 70. The device of Clause 68, wherein the coating material comprises MPC.

Clause 71. The device of Clause 68, wherein the coating material comprises MPC.

Clause 72. The device of Clause 68, wherein the filaments comprise heat-treated metallic filaments.

Clause 73. The medical device as in Clause 68, wherein the tubular member is self-expanding.

Clause 74. The medical device as in Clause 68, wherein the device exhibits an elapsed time before peak thrombin formation that is at least 1.5 times the elapsed time of the similar, uncoated device.

Clause 75. A method of treating an aneurysm formed in a wall of a parent blood vessel, the method comprising:
deploying the medical device of any preceding Clause into the parent blood vessel so that a sidewall of the medical device extends across a neck of the aneurysm, thereby causing thrombosis within the aneurysm.

Clause 76. A method of treating an aneurysm formed in a wall of a parent blood vessel of a patient, the method comprising:
deploying a coated, low-thrombogenicity flow-diverting stent in the parent blood vessel across the neck of the aneurysm, so as to treat the aneurysm; and
either (a) prescribing to the patient a reduced protocol of blood-thinning medication, in comparison to a protocol that would be prescribed to the patient if an otherwise similar but uncoated, non-low-thrombogenicity stent were deployed in the patient, or (b) declining to prescribe to the patient any blood-thinning medication.

Clause 77. The method of Clause 76, wherein the stent comprises the medical device of any preceding Clause.

Clause 78. The method of Clause 76, wherein the patient is one who has been diagnosed as being at risk of an intracranial hemorrhage.

Clause 79. The method of Clause 76, wherein the patient is one who has been diagnosed as being at risk of a cerebral hemorrhage from an aneurysm.

Clause 80. The method of Clause 76, wherein the parent blood vessel is an intracranial artery.

Clause 81. The method of Clause 76, further comprising accessing a treatment region near the aneurysm by inserting a microcatheter into the parent vessel, and delivering the stent through the microcatheter to the treatment region.

Clause 82. The method of Clause 76, wherein the stent exhibits an elapsed time before peak thrombin formation that is at least 1.5 times the elapsed time of the similar but uncoated stent.

Clause 83. A method of treating an aneurysm formed in a wall of a parent blood vessel of a patient, the method comprising:
deploying a flow-diverting stent in the parent blood vessel across the neck of the aneurysm, so as to treat the aneurysm, at least a portion of the stent being coated with an anti-thrombogenic material so that the stent exhibits an elapsed time before peak thrombin formation that is at least 1.5 times the elapsed time of an otherwise similar but uncoated stent; and
either (a) prescribing to the patient a reduced protocol of blood-thinning medication, in comparison to a protocol that would be prescribed to the patient if the otherwise similar but uncoated stent were deployed in the patient, or (b) declining to prescribe to the patient any blood-thinning medication.

Clause 84. The method of Clause 83, wherein the stent comprises the medical device of any preceding Clause.

Clause 85. The method of Clause 83, wherein the patient is one who has been diagnosed as being at risk of an intracranial hemorrhage.

Clause 86. The method of Clause 83, wherein the patient is one who has been diagnosed as being at risk of a cerebral hemorrhage from an aneurysm.

Clause 87. The method of Clause 83, wherein the parent blood vessel is an intracranial artery.

Clause 88. The method of Clause 83, further comprising accessing a treatment region near the aneurysm by inserting a microcatheter into the parent vessel, and delivering the stent through the microcatheter to the treatment region.

Clause 89. A medical device for treating an aneurysm, comprising:
a tubular member comprising a plurality of braided filaments that form a sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm; and
an anti-thrombogenic material distributed over the tubular member such that the pores are substantially free of webs formed by the material;
wherein the tubular member exhibits an elapsed time before peak thrombin formation that is at least 1.5 times the elapsed time of an identical, uncoated tubular member.

Clause 90. The medical device of Clause 89, wherein the pores have an average pore size that is less than or equal to about 500 microns.

Clause 91. The medical device of Clause 89, wherein the pores have an average pore size that is less than or equal to about 320 microns.

Clause 92. The medical device of Clause 91, wherein the pores have an average pore size that is measured using an inscribed circle diameter.

Clause 93. The medical device of Clause 89, wherein the distribution of the anti-thrombogenic material is substantially complete over the tubular member.

Clause 94. The medical device of Clause 93, wherein the anti-thrombogenic material is generally uniform over the tubular member.

Clause 95. The medical device of Clause 89, wherein the distribution of the anti-thrombogenic material is substantially complete over at least a circumferential section of the tubular member that is 5 mm or more in length.

Clause 96. The medical device of Clause 95, wherein the anti-thrombogenic material comprises an anti-thrombogenic polymer.

Clause 97. The medical device of Clause 96, wherein the anti-thrombogenic polymer comprises MPC.

Clause 98. The medical device of Clause 89, wherein the tubular member comprises a heat-set metallic braid.

Clause 99. The medical device of Clause 89, wherein the tubular member is self-expanding.

Clause 100. The medical device of Clause 89, wherein the tubular member has an open proximal end, an open distal end, and forms a lumen extending from the proximal end to the distal end.

Clause 101. The medical device of Clause 89, wherein the tubular member exhibits an elapsed time before peak thrombin formation that is at least 2.5 times the elapsed time of an identical, uncoated tubular member.

Clause 102. The medical device of Clause 89, wherein the tubular member has an expanded diameter, and an unexpanded diameter smaller than the expanded diameter, and the unexpanded diameter is 5 mm or less.

Clause 103. The medical device of Clause 102, wherein the unexpanded diameter is 3 mm or less.

Clause 104. A delivery system for treating an aneurysm, the system comprising:
an elongate core assembly comprising a tube, a wire, or a combination of a tube and a wire; and
the medical device of Clause 89 engaged with the core assembly so as to be movable via the core assembly.

Clause 105. The delivery system of Clause 104, further comprising a microcatheter configured to be implanted into a blood vessel, wherein the core assembly is configured to extend within the microcatheter.

Clause 106. The delivery system of Clause 104, further comprising a polymeric member that engages an inner wall of the tubular body and enables longitudinal force transmission from the core assembly to the tubular body.

Clause 107. A medical device for treating an aneurysm, comprising:
a tubular body configured to be implanted in a blood vessel and comprising a plurality of braided filaments, the body being expandable to an expanded state for treatment of the aneurysm, the body having a first section for spanning the neck of the aneurysm and a plurality of pores located between the filaments, the pores in the first section having a first average pore size of less than about 500 microns when the body is in the expanded state;
the first section having a substantially complete distribution of anti-thrombogenic material over the filaments;
wherein the first section is substantially free of webs formed between the braided filaments by the anti-thrombogenic material;

wherein the tubular body exhibits an elapsed time before peak thrombin formation that is at least 1.5 times the elapsed time of an identical, uncoated tubular body.

Clause 108. The medical device of Clause 107, wherein the first average pore size is less than or equal to about 320 microns.

Clause 109. The medical device of Clause 107, wherein the first average pore size is measured using an inscribed circle diameter.

Clause 110. The medical device of Clause 107, wherein the first average pore size is the average size of the pores in the first section without the anti-thrombogenic material.

Clause 111. The medical device of Clause 107, wherein the first section comprises less than an entire length of the tube.

Clause 112. The medical device of Clause 107, wherein the anti-thrombogenic material on the first section is generally uniform over the filaments.

Clause 113. The medical device of Clause 107, wherein the anti-thrombogenic material comprises an anti-thrombogenic polymer.

Clause 114. The medical device of Clause 113, wherein the anti-thrombogenic polymer comprises MPC.

Clause 115. The medical device of Clause 107, wherein the tubular body comprises a heat-set metallic braid.

Clause 116. The medical device of Clause 107, wherein the tubular body is self-expanding.

Clause 117. The medical device of Clause 107, wherein the tubular body has an open proximal end, an open distal end, and forms a lumen extending from the proximal end to the distal end.

Clause 118. The medical device of Clause 107, wherein the tubular body exhibits an elapsed time before peak thrombin formation that is at least 2.5 times the elapsed time of an identical, uncoated tubular member.

Clause 119. The medical device of Clause 107, wherein the tubular body has an expanded diameter, and an unexpanded diameter smaller than the expanded diameter, and the unexpanded diameter is 5 mm or less.

Clause 120. The medical device of Clause 119, wherein the unexpanded diameter is 3 mm or less.

Clause 121. A delivery system for treating an aneurysm, the system comprising:
an elongate core assembly comprising a tube, a wire, or a combination of a tube and a wire; and
the medical device of Clause 107 engaged with the core assembly so as to be movable via the core assembly.

Clause 122. The delivery system of Clause 121, further comprising a microcatheter configured to be implanted into a blood vessel, wherein the core assembly is configured to extend within the microcatheter.

Clause 123. The delivery system of Clause 121, further comprising a polymeric member that engages an inner wall of the tubular body and enables longitudinal force transmission from the core assembly to the tubular body.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 9B is a detailed side view of a stent mounting apparatus for use with the coating system of FIG. 6.

FIG. 9C is a detailed front view of the stent mounting apparatus of FIG. 9B.

FIG. 9D is a detailed view of a lower fixture of the stent mounting apparatus of FIGS. 9B-9C.

FIG. 20 depicts a delivery system that may be used to deliver a stent into a hollow anatomical structure, such as a blood vessel.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology. Further, although the present disclosure may refer to embodiments in which the apparatus is a stent, aspects of the embodiments disclosed herein can be used with any implantable device, such as coils, filters, scaffolds, self-expanding and balloon-expandable stents, and other devices.

In accordance with some embodiments disclosed herein, a heat-treated device (e.g., stent) is provided that comprises an even coating that is substantially free of imperfections, such as lumps, fibers, webs, and/or other obstructions in the pores of the device. Further, in some embodiments, such a device can be braided and/or have a flow diverting section.

To the Applicants' knowledge, the devices and methods disclosed herein have not been available or possible based on prior devices and methods of manufacture. In general, prior coated devices, such as stents, have demonstrated various coating imperfections and resultant disadvantages.

Among these disadvantages, "webbing," delamination, and uneven layering of coating material pose significant risks. "Webbing" of coating material occurs when the coating material spans or extends between filaments of a device to create a thin, localized film of coating material between the filaments. Delamination occurs when coating material peels away from or is not bound to the device filaments. Uneven layering of coating material can exacerbate the effects of delamination and webbing, creating large pieces of coating that do not easily dissolve or pass through a blood vessel when such pieces are dislodged. Webbing and delamination create a significant risk to proper blood flow if that coating material is dislodged or breaks free from the device filaments. If this occurs, the dislodged coating material can create or contribute to blockages in the blood vessel. This is a dangerous condition that can result from certain prior art devices and coating processes.

Figure 1:
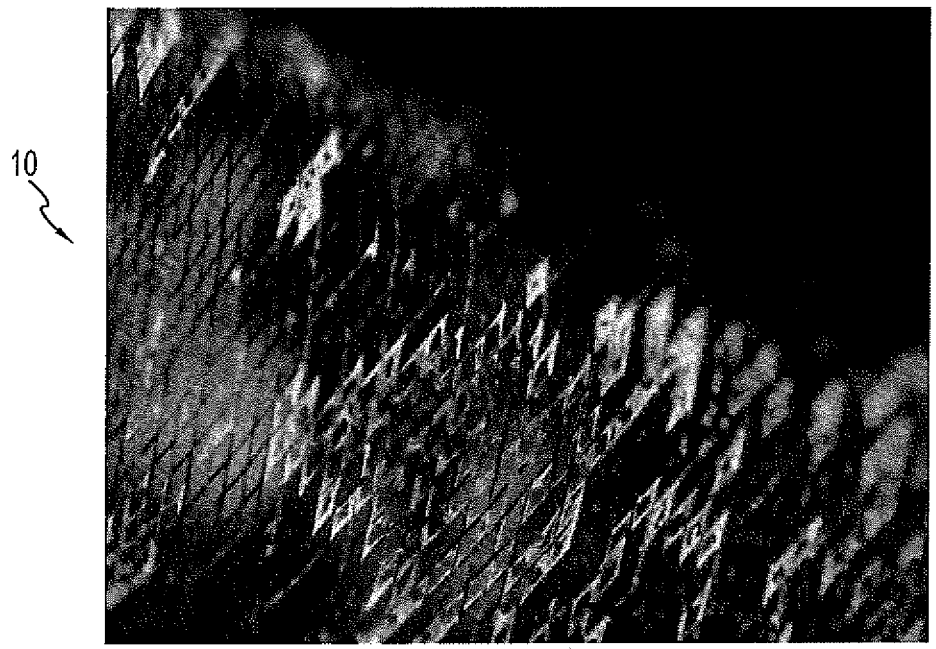
FIG. 1 is a perspective view of a device, illustrated as a stent, having a coating applied using a prior art method, illustrating webbing of the coating.

For example, referring to FIG. 1, a braided stent 10 illustrates problems that can arise when the stent 10 is coated with a coating material. As shown, the coating material (which appears in FIG. 1 as the relatively brighter portions of the stent 10) is distributed generally unevenly along the braided stent 10 and has spanned between adjacent filaments to produce "webs" or "webbing" between the filaments of the braided stent 10.

Figure 2:
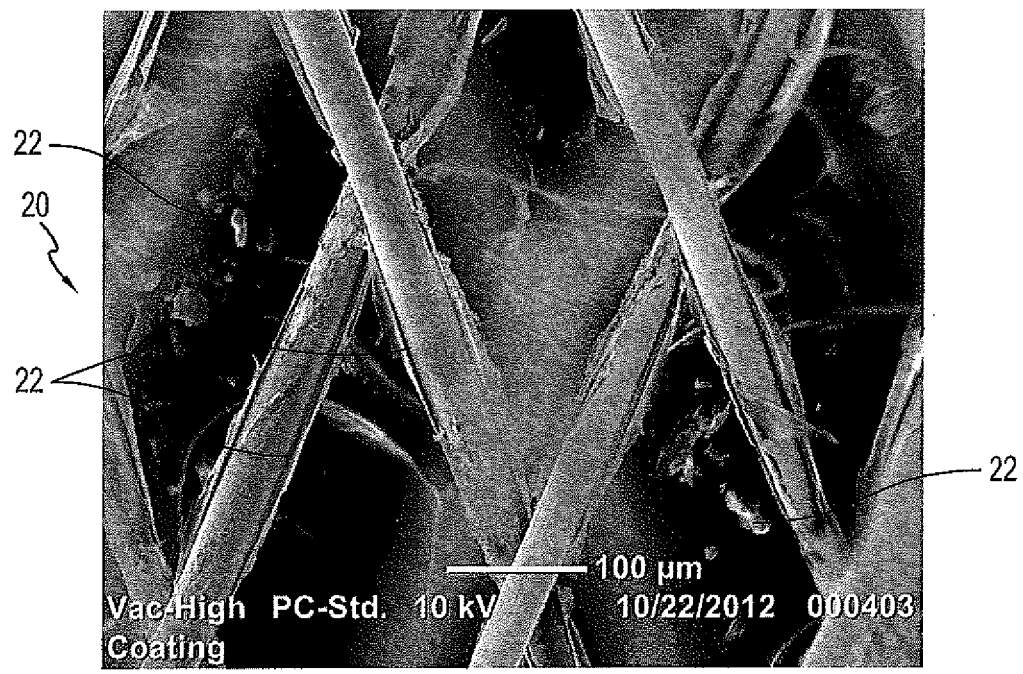
FIG. 2 is an enlarged view of a stent having a coating applied using a prior art method, illustrating delamination of the coating.
Figure 3A:
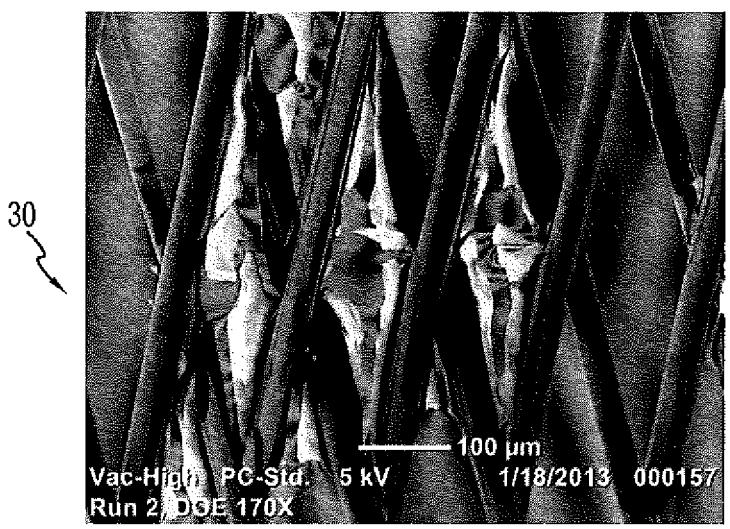
FIGS. 3A-3C are enlarged views of a stent having a coating applied using a prior art method, illustrating accumulation of excess coating material and webbing.
Figure 3B:
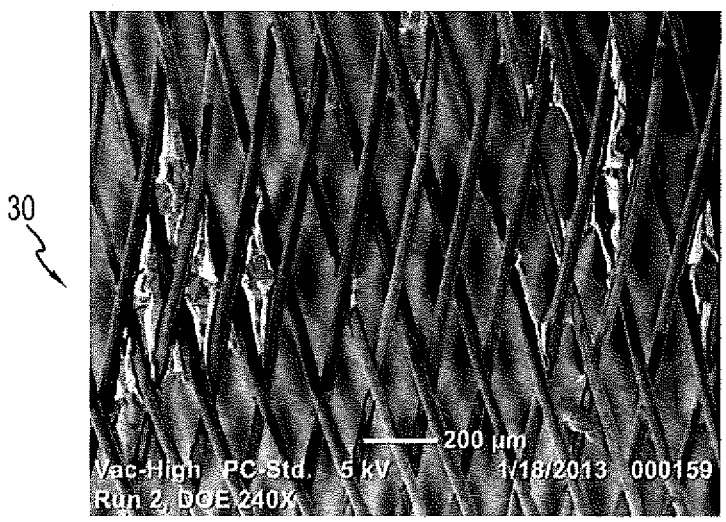
Figure 3C:
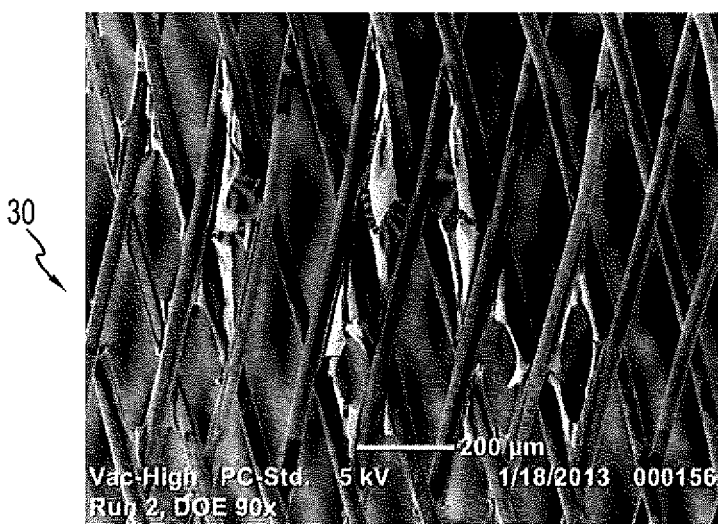

FIG. 2 is a high magnification view of a braided stent 20 coated with a coating material 22 that has delaminated. The delaminated coating material 22 can easily break free from the stent, as discussed below. FIGS. 3A-C also illustrate other views of a stent 30 having excess coating and delamination.

Typically, a braided vascular device such as a stent is braided from filaments which are formed from metal alloys and/or other high-temperature materials. The resulting braid is then heat-treated or "heat-set" at high temperature in order to reduce internal stresses in the filaments and increase the self-expanding capability of the stent. The prevalence of heat treatment and need for self-expanding properties in the manufacture of braided vascular devices and stents negates the possibility of "pre-coating" the individual filaments with a low-temperature material such as a polymer, a drug or a drug carrier and then braiding the pre-coated filaments to form a device which must then be heat-treated. Truly, a person of skill has had no expectation of successfully braiding filaments that have been pre-coated with any of the low-temperature materials that make up the bulk of useful coatings, and later heat setting the braided device to create a coated, heat-set device because of the significant damage the heat would cause to the coating.

Furthermore, no prior device or method of manufacturing known to the Applicants has been able to produce a heat-treated, coated, braided implantable device with a small pore size that is free of the disadvantages of webbing, delamination, and uneven layering of coating material, which is now possible in accordance with some implementations of the present disclosure. Again, given the exceedingly small pore size, a person of skill has had no expectation of successfully coating such a device evenly and without the disadvantages of webbing, delamination, or other coating imperfections. FIGS. 1-3C demonstrate the difficulty of coating such small-pore-size devices.

Indeed, to the present knowledge of the Applicants, no prior devices or methods of manufacture have been developed that produce a coated device (e.g., stent) having a flow diverting section that is substantially free of the disadvantages noted above. As discussed herein, a flow diverting section can have pores with a "flow diverting pore size." A "flow diverting pore size" can refer to an average pore size of pores (in at least a section of a device) that is sufficiently small enough to interfere with or inhibit fluid exchange through the pores of that section. For example, a device (e.g., stent) can have an active section or a flow diverting section with a flow diverting pore size when the pores of the section are sized to inhibit flow of blood through the sidewall into an aneurysm to a degree sufficient to lead to thrombosis and healing of the aneurysm when the tubular member is positioned in a blood vessel and adjacent to or across the neck of the aneurysm.

For example, a flow diverting pore size can be achieved when pores in the flow diverting or active section (or in the stent as a whole) have an average pore size of less than about 500 microns when the device (e.g., stent) is in the expanded state. (When "expanded state" is used herein to specify braided stent parameters such as pore sizes, the expanded state is one that the stent will self-expand to without any external expansive forces applied, and without any external longitudinal stretching or compressive forces applied. For simplicity of measurement, this expanded state can be one that the stent will self-expand to within a straight glass cylindrical tube with an inside diameter that is smaller than the maximum diameter to which the stent will self-expand in the absence of any containment or external forces.) In some embodiments, the average pore size can be less than about 320 microns. Indeed, because of such exceedingly small average pore sizes, any known prior device or attempt at manufacturing such a device resulted in substantial webbing, delamination, and uneven application of coating to the device. In contrast, some embodiments disclosed herein enable and provide a device and methods of manufacturing in which the device has a flow diverting section that is substantially free of webbing, delamination, and other coating deficiencies.

Accordingly, some embodiments provide a device, such as a braided stent, that can have a flow diverting section or other portion of the device that provides embolic properties so as to interfere with blood flow in (or into) the body space (e.g., an aneurysm) in (or across) which the device is deployed. The porosity and/or pore size of one or more sections of the device can be selected to interfere with blood flow to a degree sufficient to thrombose the aneurysm or other body space.

For example, some embodiments provide a device (e.g., stent) that can be configured to interfere with blood flow to generally reduce the exchange of blood between the parent vessel and an aneurysm, which can induce thrombosis of the aneurysm. A device (or a device component, such as a sidewall of a stent or a section of such a sidewall) that thus interferes with blood flow can be said to have a "flow diverting" property.

Additionally, in some embodiments, a device (e.g., stent) can be provided with a porosity in the range of 5%-95% may be employed in the expanded braid. In some embodiments, a porosity in the range of 30%-90% may be employed. Further, a porosity in the range of 50%-85% may be employed.

Further, in some embodiments, a device (e.g., stent) can be provided with a pore size in the range of 20-300 microns (inscribed diameter). In some embodiments, a pore size in the range of 25-250 microns (inscribed diameter) may be employed. In some embodiments, a pore size in the range of 50-200 microns (inscribed diameter) may be employed.

Methods of treatment and methods of manufacturing embodiments of the devices (e.g., stents) disclosed herein are also provided. Therefore, various embodiments of the devices disclosed herein address the problems and complications associated with unevenly and improperly coated devices (e.g., stents) and provide novel processes for manufacturing and using such devices.

Some embodiments of processes disclosed herein comprise mounting or maintaining a braided device (e.g., stent) in a longitudinally stretched configuration during the coating process. Such a device can have an expanded configuration in which the pores thereof are generally circumferentially elongated, which results in a decreased pore size or a relatively "closed" configuration. In contrast, the pore size is increased or in a relatively "open" configuration when the device is in the longitudinally stretched configuration. In the longitudinally stretched configuration, many, if not all, of the pores of the device can be opened to an enlarged pore size, or to a generally maximum pore size.

For example, in some embodiments, the longitudinally stretched configuration can open the pores by orienting the individual filaments of the device to create a pattern of open-pore quadrilaterals, such as squares, rectangles, parallelograms, rhombuses, trapezoids, etc., which can allow the pore size to be generally maximized. Further, the quadrilaterals can be formed by filaments that cross at angles from about 0° to about 15° from a right angle. In some embodiments, the angles can be from about 0° to about 10° from a right angle. In some embodiments, the angles can be from about 0° to about 5° from a right angle. Additionally, in some embodiments, the filaments can form right-angled quadrilaterals, such as squares and rectangles, which allows the pore size to be maximized. However, not every pore shape circumscribed by the filaments may be a right-angled quadrilateral, and some variation between pores in the same or different sections of a device is possible.

Further, some embodiments of processes disclosed herein comprise dipping a longitudinally stretched braided device (e.g., stent) in a solvent and thereafter "air knifing" the dipped device to remove or blow off any excess solvent from the device. The air jet(s) of the air knife(s) can be applied in a direction that is generally transverse, such as orthogonal, relative to the longitudinal axis of the device. The air knife can be stationary while the device is moved, or it can move along or about the device as the device remains stationary.

Additionally, some embodiments also provide a coating fixture which can be used during the coating (e.g., dipping, spraying, etc.) processes to optimize the coating and drying process and prevent inadvertent wicking of the coating material away from the coated device (e.g. stent), which can result from undesired contact with the coated device (e.g., stent) during the process. Some embodiments of the coating fixture can be both rigid and/or lightweight. Further, in some embodiments, the coating fixture can comprise first and second ends that engage with corresponding ends of the device and a fixture body that extends between the first and second ends and outside of a device lumen when the device is mounted to the fixture. The first and second ends can be spaced apart sufficiently to maintain the device in a longitudinally stretched configuration when mounted on the cantilevered fixture.

The device (e.g., stent) can take the form of a vascular occluding device, a revascularization device and/or an embolization device. In some embodiments, the device can be an expandable stent made of two or more filaments. The filaments can be formed of known flexible materials including shape memory materials, such as nitinol, platinum and stainless steel. In some embodiments, the filaments can be round or ovoid wire. Further, the filaments can be configured such that the device is self-expanding. In some embodiments, the device can be fabricated from a first group of filaments made of platinum alloyed with 8% tungsten, and a second group of filaments made of 35N LT (cobalt nickel alloy, which is a low titanium version of MP35N alloy). In other embodiments, one or more of the filaments can be formed of a biocompatible metal material or a biocompatible polymer.

The wires or filaments can be braided into a resulting lattice-like structure. In at least one embodiment, during braiding or winding of the device (e.g., stent), the filaments can be braided using a 1-over-2-under-2 pattern. In other embodiments, however, other methods of braiding can be followed, without departing from the scope of the disclosure. The device can exhibit a porosity configured to reduce haemodynamic flow into and/or induce thrombosis within, for example, an aneurysm, but simultaneously allow perfusion to an adjacent branch vessel whose ostium is crossed by a portion of the device. As will be appreciated, the porosity of the device can be adjusted by "packing" the device during deployment, as known in the art. The ends of the device can be cut to length and therefore remain free for radial expansion and contraction. The device can exhibit a high degree of flexibility due to the materials used, the density (i.e., the porosity) of the filaments, and the fact that the ends of the wires or filaments are not secured to each other.

Information regarding additional embodiments, features, and other details of the devices, methods of use, and other components that can optionally be used or implemented in embodiments of the occlusion devices described herein, can be found in Applicants' co-pending applications U.S. patent application Ser. No. 12/751,997, filed on Mar. 31, 2010; Ser. No. 12/426,560, filed on Apr. 20, 2009; Ser. No. 11/136,395, filed May 25, 2005; Ser. No. 11/420,025, filed May 24, 2006; Ser. No. 11/420,027, filed May 24, 2006; Ser. No. 12/425,604, filed Apr. 17, 2009; Ser. No. 12/896,707, filed Oct. 1, 2010; 61/483,615, filed May 6, 2011; 61/615,183, filed Mar. 23, 2012; Ser. No. 13/614,349, titled Methods and Apparatus for Luminal Stenting, filed on Sep. 13, 2012 (reference HKN-02608 (1), 080373-0366); Ser. No. 13/692,021, titled Methods and Apparatus for Luminal Stenting, filed on Dec. 3, 2012 (reference HKN-02608 (2), 080373-0377); and Ser. No. 13/664,547, titled Methods and Apparatus for Luminal Stenting, filed on Oct. 31, 2012 (reference HKN-02608 (3), 080373-0498); the entireties of each of which are incorporated herein by reference.

Figure 4:
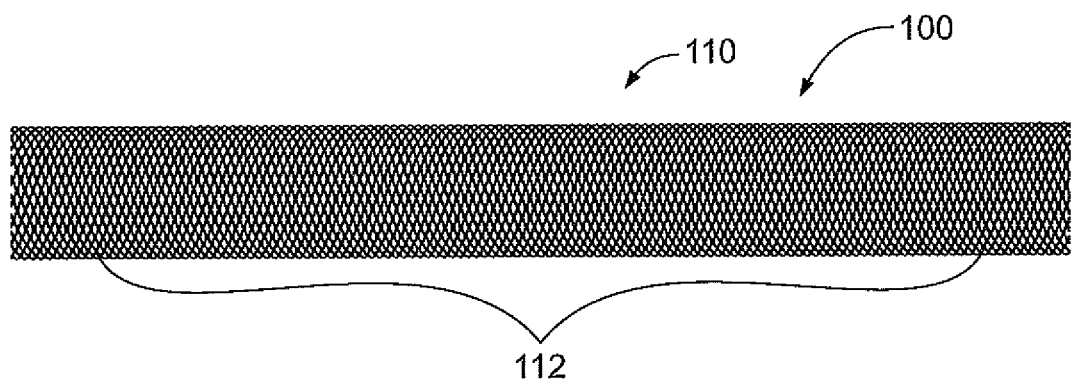
FIG. 4 is a side view of a stent comprising a coating, according to some embodiments.

FIG. 4 illustrates a tubular, self-expanding device, shown as a stent 100, comprising a coating 110 disposed along at least a portion thereof. The tubular stent 100 comprises an elongate hollow body which can be formed from a plurality of braided filaments. Some embodiments disclosed herein can comprise a coating along the entire length of the stent or merely along only a portion thereof. The stent 100 can comprise a flow diverting portion 112. The flow diverting portion 112 can comprise a plurality of pores that have a flow diverting pore size; instead of or in addition to this property, the flow diverting portion 112 can have a flow diverting porosity. The flow diverting portion 112 can comprise a portion of the stent 100, or the entire stent. The flow diverting pore size can be an average pore size within a relevant portion of the stent, e.g. within the flow diverting portion 112 or a portion thereof, or a "computed" pore size, one that is computed from measured or nominal basic stent parameters such as braid angle, number of filaments, filament size, filament diameter, stent diameter, longitudinal picks per inch, radial picks per inch, etc. Such a computed pore size can be considered to be one type of average pore size. The flow diverting pore size can be within a size range that that interferes with or inhibits blood flow through the sidewall of the stent 100, for example, between the parent vessel and an aneurysm sufficient to induce or lead to thrombosis of the aneurysm. The coating can be disposed partially or entirely along the flow diverting portion 112, or along another portion of the stent 100.

In some embodiments, the pores of the flow diverting portion 112 can have an average pore size of less than 500 microns (inscribed diameter), or in the range of 20-300 microns (inscribed diameter). Further, the average pore size can be in the range of 25-250 microns (inscribed diameter). Furthermore, the average pore size can be in the range of 50-200 microns (inscribed diameter). The stent 100 can be expandable from an unexpanded diameter to an expanded diameter; the unexpanded diameter can optionally be 5 mm or less, or 4 mm or less, or 3 mm or less, or 2 mm or less, or other unexpanded diameters, and/or the expanded diameter can optionally be 2 mm or more, or 3 mm or more, or 4 mm or more, or 5 mm or more, or other expanded diameters. The unexpanded diameter can be less than the expanded diameter.

The average pore size of the pores in the flow diverting portion 112 can be the average size of the pores measured with or without coating material disposed thereon. Thus, the average pore size of the flow diverting portion of a bare stent can be within the flow diverting ranges. Further, the average pore size of the flow diverting portion of a coated stent can be within the flow diverting ranges. Furthermore, the flow diverting portion 112 can comprise pores having sizes above or below the range of the average pore size.

Figure 5A:
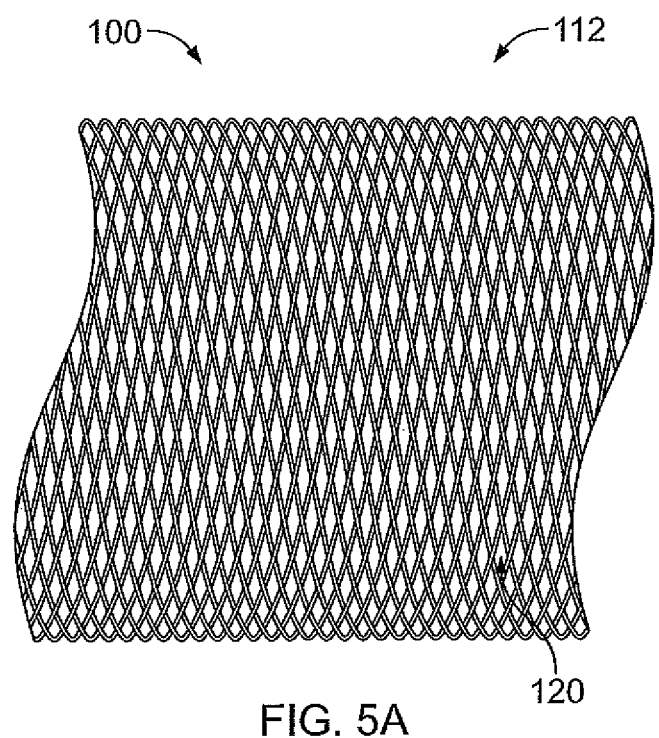
FIG. 5A is an enlarged view of the stent shown in FIG. 4, according to some embodiments.

FIG. 5A illustrates an enlarged view of a section of the flow diverting portion 112 of the stent 100. In this embodiment, the flow diverting portion 112 comprises a plurality of filaments 120 that are braided together to form the tubular body of the stent 100. FIG. 5A illustrates the self-expanding stent 100 in an expanded or relaxed state. In this expanded or relaxed state, the filaments 120 cross each other to form the pores of the stent 100.

Figure 5B:
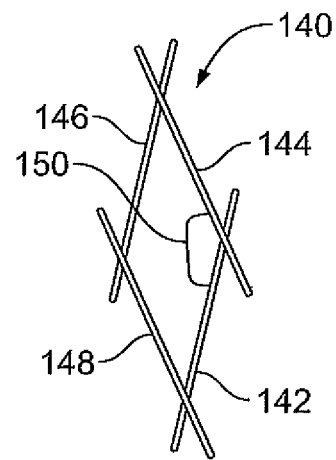
FIGS. 5B-5C are detail views of a pore of the stent of FIG. 4, in various conditions.

FIG. 5B illustrates a single pore 140 of the flow diverting section 112 when in the relaxed state. The pore 140 is formed by a plurality of filaments 142, 144, 146, and 148. As shown, the filaments 142, 144 cross each other to form an obtuse angle 150. In some embodiments, the obtuse angle 150 can be from about 110° to about 170°. Further, the obtuse angle 150 can be from about 120° to about 165°. Further, the obtuse angle 150 can be from about 130° to about 160°, and in some embodiments, the obtuse angle 150 can be about 150°.

Figure 5C:
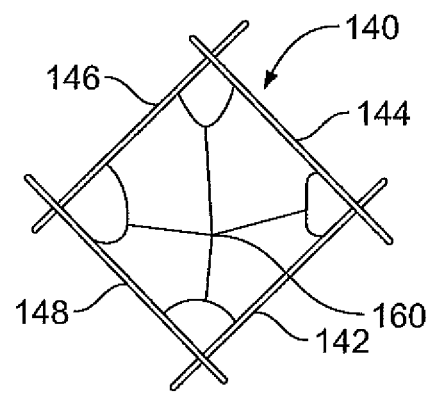

Accordingly, the size or configuration of the pore 140 is "closed" or relatively small in the expanded or relaxed state shown in FIG. 5B when compared with the relatively "open" size of the pore 140 when the stent 100 is in a longitudinally stretched configuration, as shown in FIG. 5C. FIG. 5C illustrates that the filaments 142, 144, 146, and 148 each cross each other at angles 160 that approximate a right angle, e.g. within from about 0° to about 15° from a right angle. In some embodiments, the angles 160 can be from about 0° to about 10° from a right angle. In some embodiments, the angles 160 can be from about 0° to about 5° from a right angle.

Additionally, in order to maximize the pore size, in some embodiments, the filaments can form right-angled quadrilaterals, such as squares and/or rectangles. However, not every pore shape circumscribed by the filaments may be a right-angled quadrilateral, and some variation between pores in the same or different sections of a stent is possible.

A device can be prepared according to some embodiments by braiding a plurality of filaments to form a braided stent, filter, or other braided device. The device can then be cleaned and heat treated, if necessary, to impart desired characteristics to the device. Thereafter, the device can be coated using aspects of the methods disclosed herein.

Figure 6:
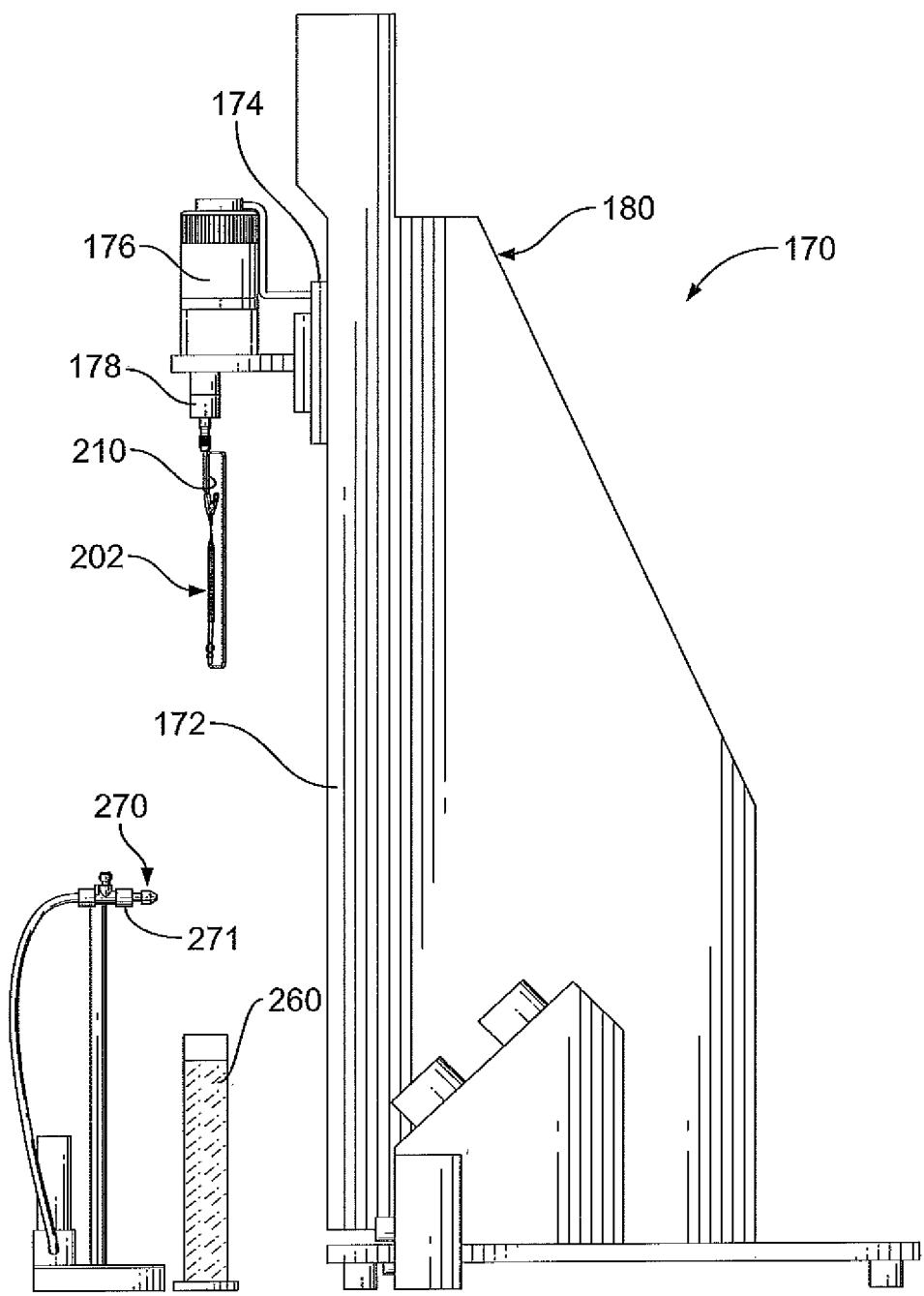
FIG. 6 is a side view of a coating system having a stent mounted thereon in a first position in preparation for coating the stent, according to some embodiments.

FIGS. 6-12 illustrate aspects of a coating apparatus and method that can be used in some embodiments to coat the stent 100, or any other embodiments of stents or other devices disclosed herein. FIG. 6 illustrates a coating system 170 that generally comprises a handling system 180, a mounting apparatus 210 that is held by the handling system 180 and in turn holds the stent 202, an open-topped container (e.g., a beaker) of coating solution 260, and an air knife 270.

The handling system 180 is generally configured to rotate and move the stent 202 and mounting apparatus 210 vertically up and down. Thus the handling system 170 includes a powered linear actuator 172 that is oriented vertically and further includes a carriage 174 that can move up and down on, and under the power of, the linear actuator 172. On the carriage 174 is mounted an electric motor 176; when powered the motor 176 rotates a chuck 178. The chuck 178 detachably grips an upper end of the mounting apparatus 210 so that the motor 176 rotates the mounting apparatus 210 and stent 202 about a generally vertical axis when the motor 176 is energized.

The coating solution 260 is positioned beneath the motor 176 and mounting apparatus 210, and aligned generally with the mounting apparatus 210 and the rotational axis of the motor 176. Therefore, a downward movement of the carriage 174 (and with it the motor 176 and mounting apparatus 210) along the linear actuator 172 will cause the lower portions of the mounting apparatus 210 and stent 202 to be immersed in the coating solution 260 (see FIGS. 7A, 7B).

The air knife 270 comprises a nozzle 271 that is connected via a hose to a source of pressurized air or other pressurized gas (not shown). The nozzle 271 is positioned and oriented so that, upon activation of the air knife 270, the nozzle directs an air jet or air stream 272 (see FIG. 8B) that strikes the stent 202 when the carriage 174 and motor 176 are positioned along or moving through a particular "air knifing" region of the linear actuator 172.

The coating system 170 can be used to coat a stent generally as follows. The process begins with the coating system in the start position shown in FIG. 6. The linear actuator 172 is energized to lower the carriage 174, and with it the motor 176, mounting apparatus 210 and stent 202, until the lower portions of the apparatus 210 and stent 202 are submerged in the coating solution 260 (see FIGS. 7A, 7B). The mounting apparatus 210 and stent 202 are left in the solution 260 momentarily before the linear actuator 172 is energized again to raise the stent 202, now wet with coating solution, toward the air knife 270. When the stent 202 is fully out of the coating solution 260, the actuator 172 pauses for a brief pre-drying period before moving the stent 202 into the air stream 272. Once the pre-drying period is over, the stent is moved upward into the air stream 272. While the air stream 272 is striking the stent 202, the stent is simultaneously rotated and reciprocated vertically (via the motor 176 and actuator 172, respectively) relative to the nozzle 271 so that the stent is moved back and forth through the air stream. Thus, substantially all of the outer surface of the stent 202 is moved across the nozzle 271 and exposed to the air stream 272 during the knifing process, and any excess coating solution is blown off.

Figure 9A:
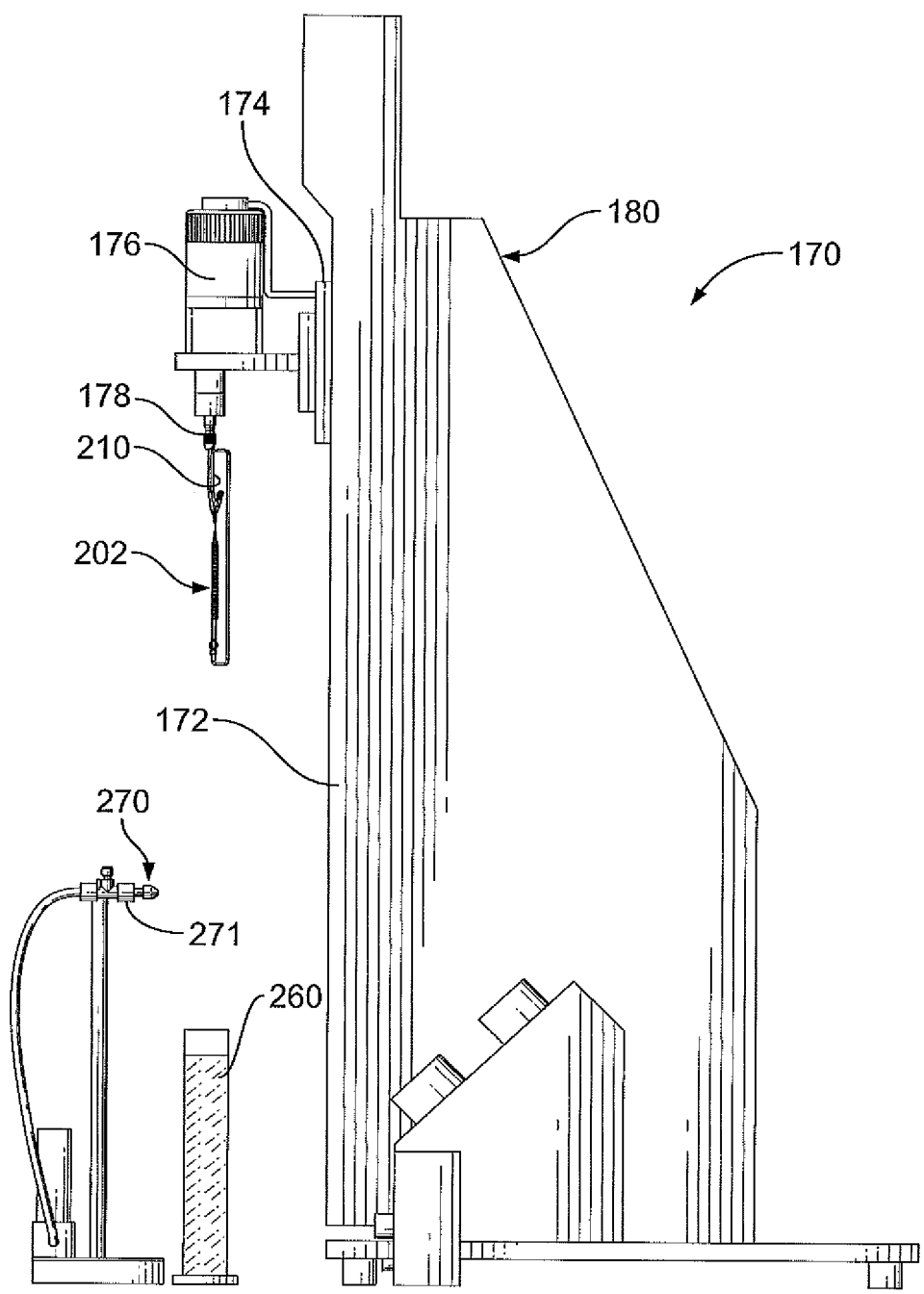
FIG. 9A is a side view of the coating apparatus of FIG. 6, wherein the stent has been returned to the first position.

After air knifing is complete, the stent 202 is then raised out of the stream 272 via the actuator 172 (and/or the air knife 270 is deactivated), as shown for example in FIG. 9A. The mounting apparatus 210 is now removed from the motor 176 by loosening the chuck 178. The stent 202 can be allowed to dry further while still mounted on the mounting apparatus, either at room temperature or at elevated temperature in a drying oven. Once the stent is dry, it can be removed from the mounting apparatus 210 and cut to its final length by trimming off one or both ends of the stent.

More specific aspects of the coating system 170 and methods of coating will now be discussed in greater detail.

Figure 10:
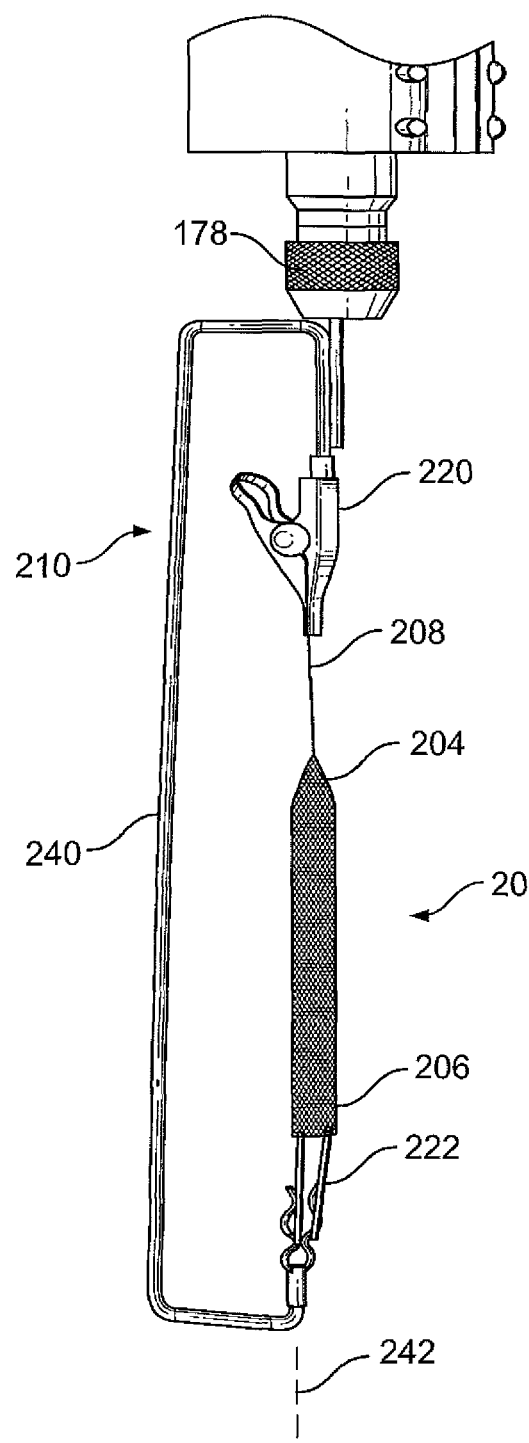
FIG. 10 is a side view of the mounting apparatus of FIGS. 9B-9D, with a stent mounted thereon.
Figure 11:
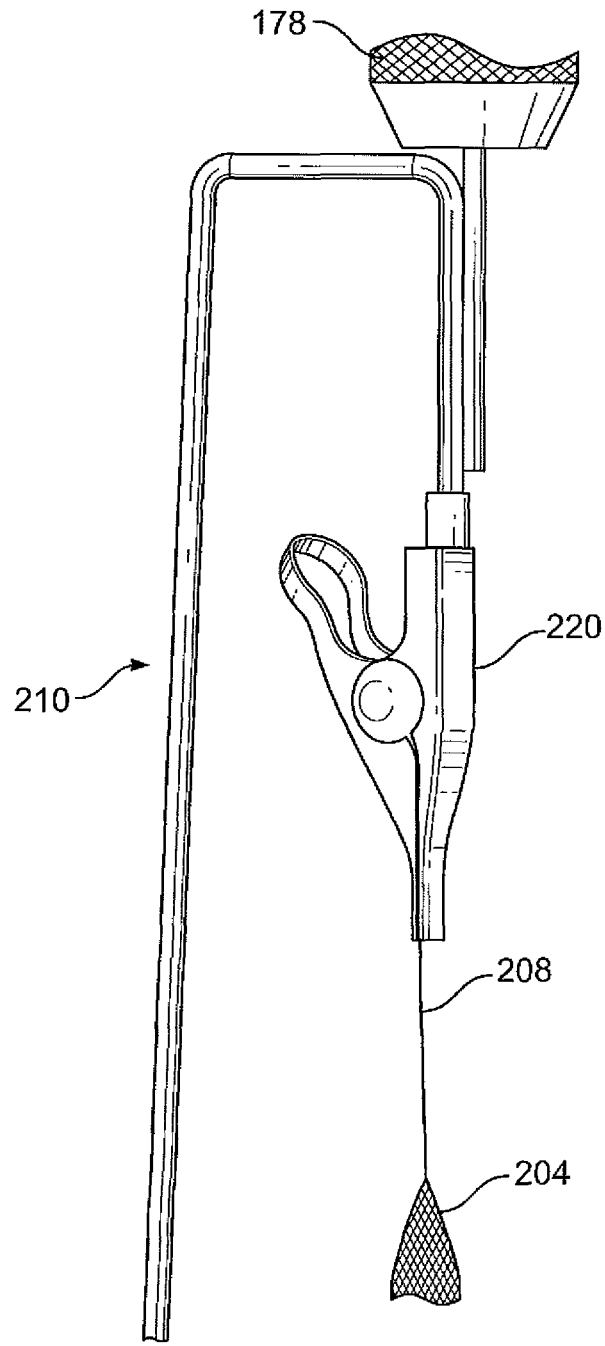
FIG. 11 is an enlarged view of an upper bracket of the mounting apparatus of FIGS. 9B-10, according to some embodiments.
Figure 12:
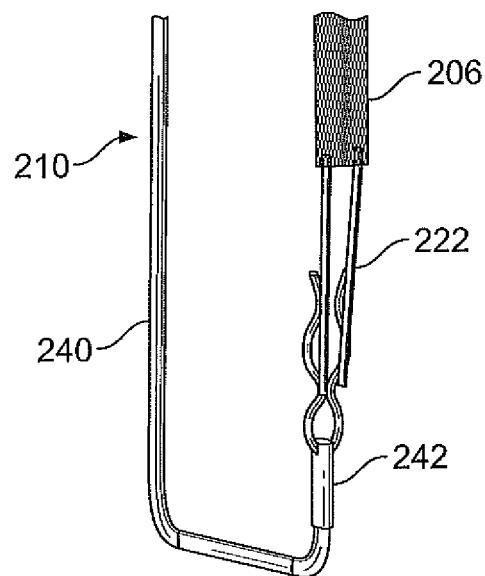
FIG. 12 is an enlarged view of a lower bracket of the mounting apparatus of FIGS. 9B-11, according to some embodiments.

Enlarged views of the mounting apparatus 210, with the stent 202 mounted thereon, are illustrated in FIGS. 10-12. The stent 202 comprises a tubular braid (which can be similar to any of the herein-described embodiments of the stent 100), with an upper portion 204 and a lower portion 206. As shown in FIGS. 10-11, in order to facilitate attachment to the mounting apparatus 210, the stent upper portion 204 can be closed and comprise an elongate wire 208 that extends therefrom. For example, in some embodiments, wire 208 can be welded to the stent upper portion 204 to close the stent 202 and form a cone at its upper portion 204. The elongate wire 208 can be engaged by an upper fixture 220 of the mounting apparatus 210. The upper fixture 220 can comprise an alligator clip that can grip the wire 208, or a hook or pin around which the wire 208 can be wound, or other mechanical fastener operative to securely engage the wire 208.

Further, as shown in FIGS. 10 and 12, the stent lower portion 206 can comprise an open end. The stent lower portion 206 can be engaged by a lower fixture 222 of the mounting apparatus 210. The lower fixture 222 can comprise an alligator clip, a hook, or other mechanical fastener operative to securely engage the stent lower portion 206. For example, FIG. 12 illustrates a pair of deflectable prongs that can be inserted into a lumen of the stent 202 and exert a biasing force such that ends of the deflectable prongs engage the inner wall of the stent lower portion 206. Each prong includes near its upper tip an outwardly- and downwardly-projecting barb 223 (FIG. 9D) that is received in and projects through a pore of the stent 200, to facilitate a secure grip of the lower portion 206.

The mounting apparatus 210 (see also FIGS. 9B-9D) can comprise an elongate backbone 240 that interconnects the upper and lower fixtures 220, 222. The upper and lower fixtures 220, 222 can define an axis 242 extending therebetween, along which an axis of the stent 200 can be generally aligned when mounted on the fixtures 220, 222. The elongate backbone 240 can comprise a relatively thin, but nonetheless sufficiently rigid, wire, for example a single stainless steel wire of 0.055 inch diameter.

The depicted mounting apparatus 210 incorporates a number of design features that enable high-precision coating of the stent 100/202. The upper and lower fixtures 220, 222 are spaced apart so that the stent is held in a longitudinally stretched configuration and the pores are caused to take on the "open" configuration shown in FIG. 5C, characterized by the formation of approximately right angles between the filaments. With the pores so opened, any webs can be blown out of the pores without need for a high-pressure air stream which presents a risk of blowing too much of the coating solution off the stent. Substantially no portion of the mounting apparatus 210 protrudes into the lumen of the stent (the sole exception being the tips of the prongs of the lower fixture 222, which extend into a portion of the stent that will be trimmed away after coating is complete). As a result, the mounting apparatus does not interfere with the flow of the air stream 272 through the stent during the knifing process. The only portion of the mounting apparatus 210 that is ever situated between the nozzle 271 and the stent during the knifing process is the backbone 240. However, the effect of this is mitigated by (1) the narrow, thin profile of the backbone 240, (2) the offset between the backbone 240 and the stent, which allows the portion of the stent that is "shadowed" by the backbone to be impacted effectively by the air stream 272 immediately before and after the backbone passes through the air stream, and (3) the fact that the backbone 240 interrupts the air stream 272 only momentarily, once per revolution of the stent, as opposed to the constant airflow interruption that would result from an apparatus member that extends through the stent lumen. The absence of any mounting apparatus member 210 in the stent lumen, and the offset between the backbone 240 and the stent, further contribute to precision coating by reducing or eliminating the possibility of the stent contacting the backbone 240 or any luminally-protruding apparatus member as the stent deflects in reaction to air stream 272 striking the stent. Such contact can wick coating solution away from the stent and degrade the quality of the resulting coating. The tension induced in the stent by virtue of being longitudinally stretched in the mounting apparatus 210 also assists in reducing/eliminating such undesired contact resulting from deflection of the stent. The configuration of the mounting apparatus 210 substantially aligns the axis 242, which is approximately the axis of rotation of the apparatus 210 and the stent when the knifing process is underway, with the central longitudinal axis of the stent. Accordingly, the stent is rotated substantially "on center" during the knifing process, which helps promote an even distance between the stent and the nozzle 271 (and even application of the air stream 272 to the stent) through 360 degrees of rotation of the stent. In addition, the configuration of the lower fixture 222 "places" minimal weight of the mounting apparatus 210 in a location remote from the point of attachment of the apparatus 210 to the chuck 178. It was found that using a clip-and-wire arrangement similar to the upper fixture 220 and upper portion 204 placed too much weight too far from the chuck 178, which induced a "pendulum effect" in the mounting apparatus 210 in reaction to the incident air stream 272, as the apparatus 210 deflected off axis and the resulting back-and-forth motion of the apparatus 210 was magnified by the mass of the relatively heavy lower fixture and its location a relatively long distance away from the chuck 178. A large pendulum effect pulls the stent off-center during knifing and results in uneven application of the air stream 272 to the stent. In comparison, the lighter weight and shorter length of the lower fixture 222 employed in the depicted mounting apparatus 210 reduces the pendulum effect to acceptable levels or eliminates it altogether. The relatively thin profile of the members constituting the mounting apparatus (particularly the backbone 240) also reduces the pendulum effect by reducing the force of the air stream 272 impinging on the mounting apparatus. The depicted lower fixture 222 also keeps the lower portion 206 of the stent open, which allows for more effective draining of excess coating solution from the stent after the stent has been raised out of the coating solution 260, as compared to the conical configuration of the stent upper end 204 employed with the upper fixture 220. The overall cantilevered configuration of the mounting apparatus 210 facilitates dipping the stent in the coating solution 260, and subsequently raising the stent toward the air knife 270 in a simple straight line, while incorporating a brief pre-drying pause before the knifing process begins.

Figure 7A:
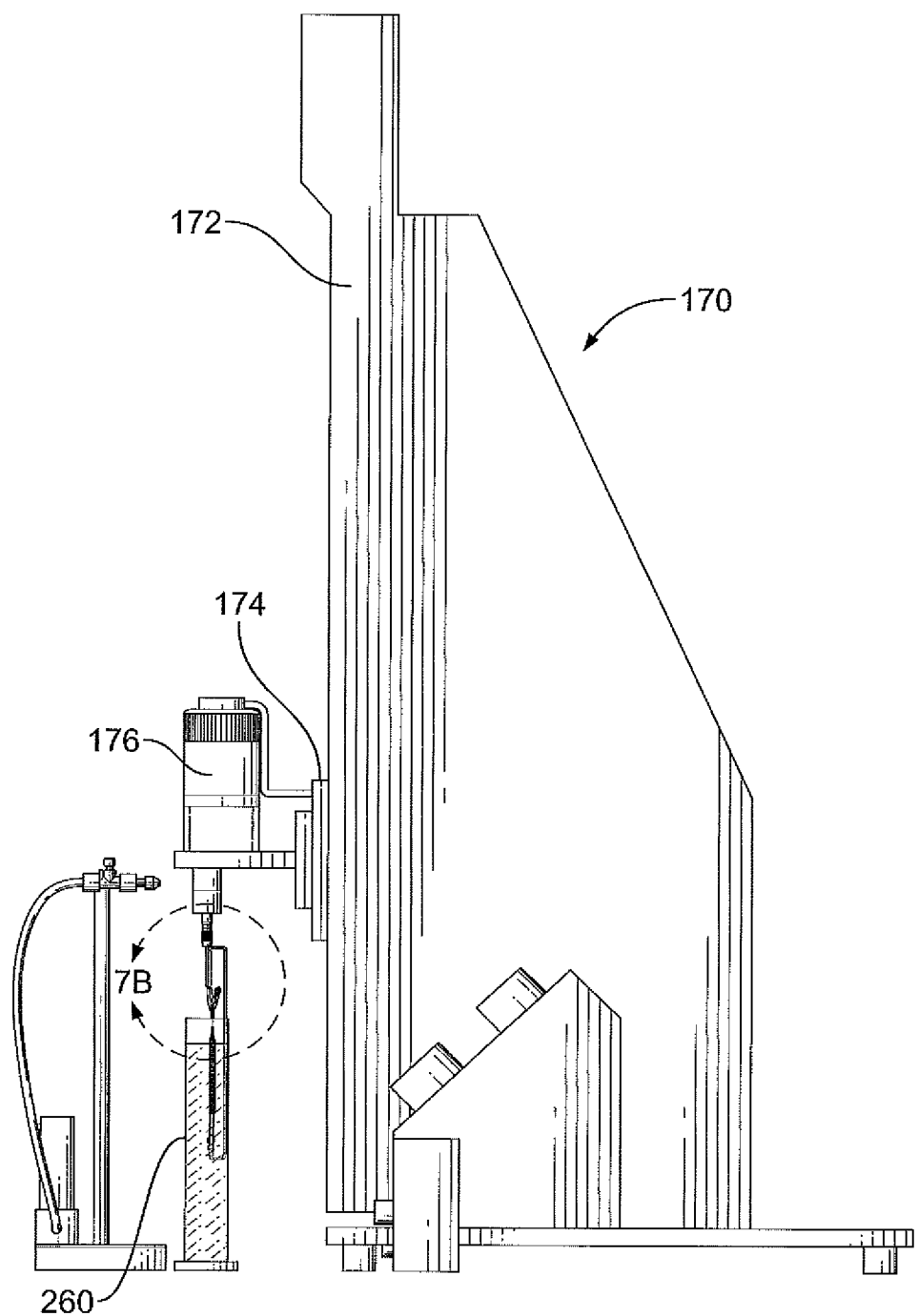
FIG. 7A is a side view of the coating system of FIG. 6, wherein the stent has been immersed in a coating solution, according to some embodiments.
Figure 7B:
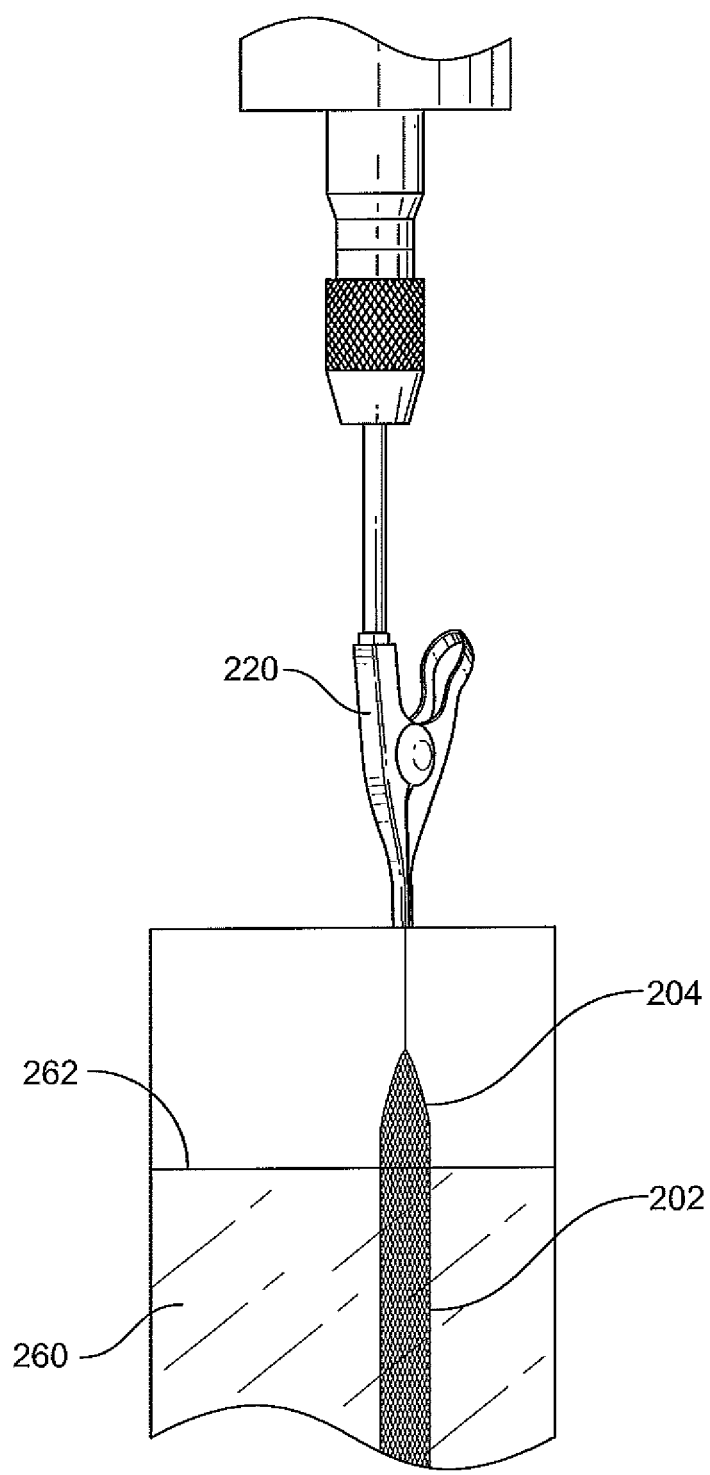
FIG. 7B is a detail view of the dipping procedure near an upper end of the stent being dipped.
Figure 8A:
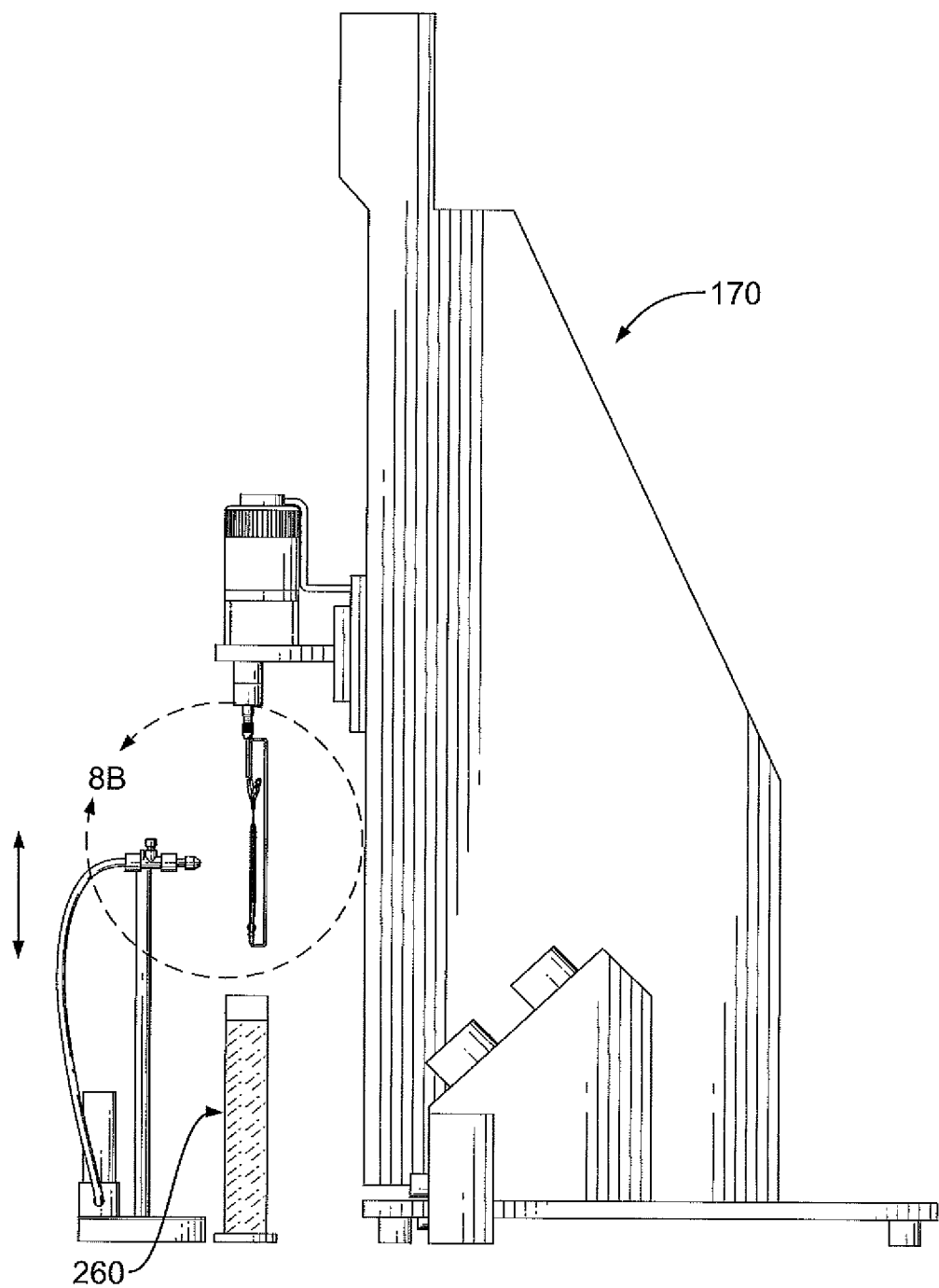
FIG. 8A is a side view of the coating apparatus of FIG. 6, wherein the stent is removed from the coating solution and coating solution is removed, according to some embodiments.
Figure 8B:
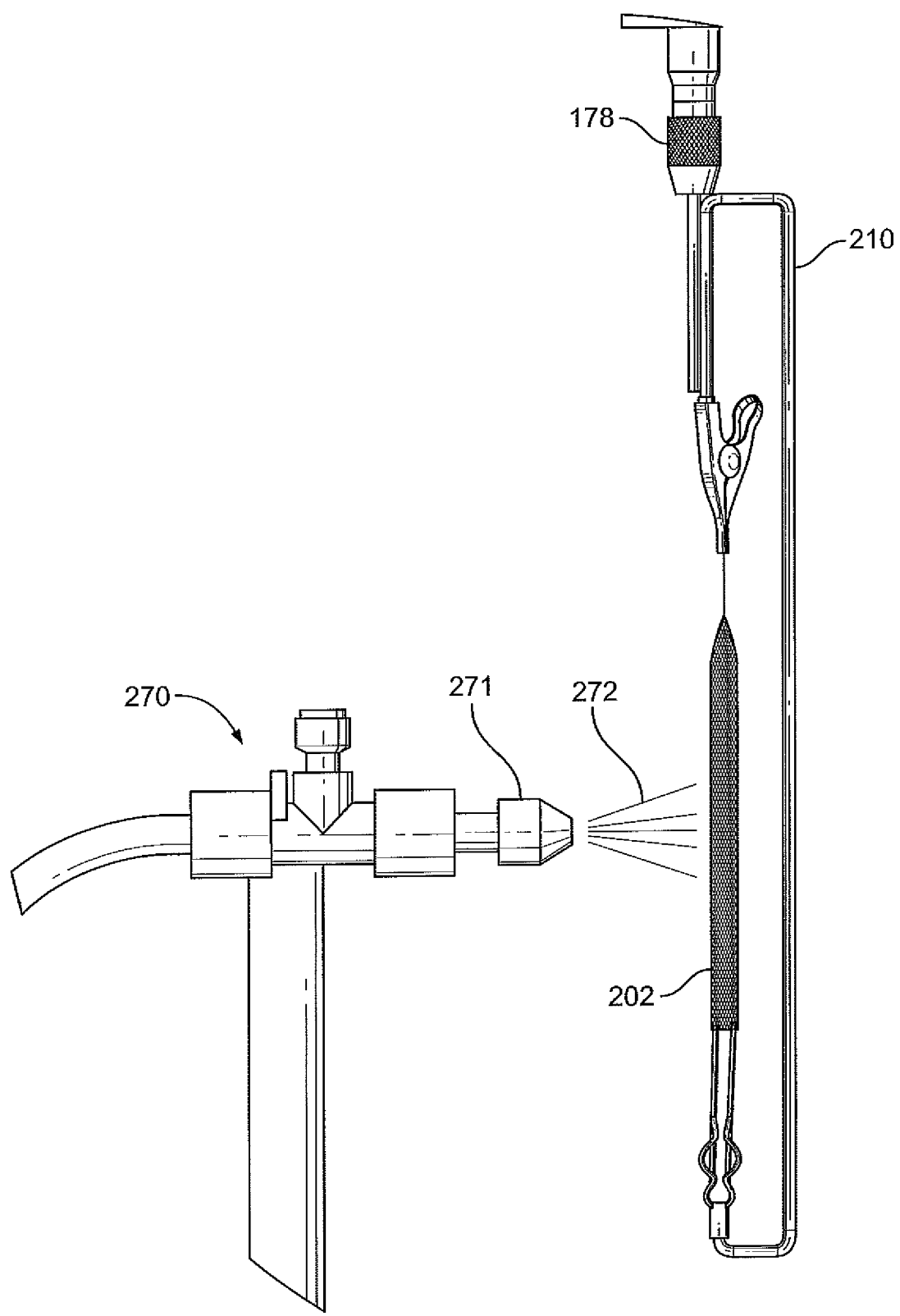
FIG. 8B is a detail view of an air knifing procedure being carried out on the stent with the coating system of FIG. 6.

As illustrated in the enlarged view of the dipping procedure shown in FIG. 7B, the stent 202 is lowered into the coating solution 260 until the stent upper portion 204 reaches the top surface 262 of the coating material 260, but the stent upper portion 204 is not submersed into the coating material 260. Accordingly, the conical upper portion 204 remains dry. The Applicants discovered that, when the conical upper portion is left dry and uncoated, the coating solution drains more effectively from the stent after it is raised out of the solution 260. This more effective draining of the solution in turn facilitates a neater, more precise blow-off of the solution from the stent and better coating performance.

In a preferred embodiment of the above-described method and apparatus for coating a stent, the dimensions and process parameters shown in Table 1 below can be used for constructing the mounting apparatus 210 and performing the method.

TABLE 1

| Mounting Apparatus Dimensions (FIGS. 9B, 9C, 9D) | | Process Parameters | |
| --- | --- | --- | --- |
| Dimension | Size | Parameter | Value |
| A | 6.5" | Air knife pressure | 12 PSI |
| B | 0.56" | Air knife flow rate | Approx. 26 SLPM |
| C | 0.7" | Distance from nozzle to stent | 60 mm |
| D | 1.25" | Nozzle inside diameter | 2.0 mm |
| E | 2.9" | Rotation speed | 100 RPM |
| F | 2.5" | Reciprocation speed | 24 mm/s |
| G | 0.5" | Reciprocation: number of passes through air stream | 5 |
| H | 0.055" (wire diameter) | Amount of longitudinal stretch of stent, from rest | Approx. 2x |
| I | 0.353" | Stent braid angle when stretched | Approx. 90 degrees |
| J | 10 degrees | Pre-drying time | 10-15 seconds |
| K | 1.0" | Drying temperature | 60 degrees C |
| L | 0.032" (diameter) | Drying time | 15 minutes |
| | | Process ambient temperature and humidity | Room temperature and humidity |
| | | Coating solution temperature | Room temperature |
| | | Pressurized air source | Standard "shop" air with in-line air dryer |

Some of these parameters can be varied in other embodiments. For example, the air knife pressure could be 6-18 PSI, or 10-14 PSI; the distance from the nozzle to the stent could be 20-80 mm, or 40-70 mm; the stent rotation speed could be 50-150 RPM, or 80-120 RPM; the reciprocation speed could be 10-40 mm/s, or 18-30 mm/s; the amount of longitudinal stretch of the stent could be 1.5x-3x; the drying temperature could be 50-80 degrees C.; and/or the drying time could be 5-60 minutes. Although the air knife 270 is described as blowing air on the stent, other gases could be employed, such as nitrogen, argon or other relatively inert gases.

Other variations of the method and apparatus are possible. For example, multiple nozzles or gas sources could be used in the air knife 270 instead of the single nozzle 271 depicted and described above. The air knife 270 can move during the knifing process while the stent 202 remains stationary, rather than the reverse as described above. The backbone 240 can be made in a constant thickness or diameter that varies somewhat from that specified herein, or the backbone 240 can taper. For example, the backbone 240 can taper from a larger size at its upper end to a smaller size at its lower end.

Further, although dip coating and removal of excess coating material by air knife are discussed above, other coating methods can be implemented. For example, in some embodiments, the stent can be coated using a spray coating process. In spray coating, the coating material may be applied to the device using a spray coater.

Figure 13:
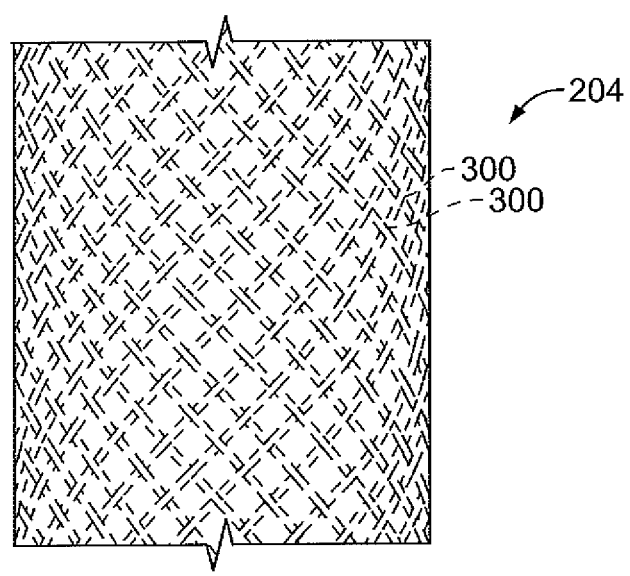
FIG. 13 is an enlarged view of a stent mounted on the mounting apparatus of FIGS. 9B-12 in a stretched configuration, according to some embodiments.

Referring now to FIG. 13, an enlarged view of the stent 204 is shown in its longitudinally stretched configuration, as achieved when engaged by the mounting apparatus 210 during the coating process. As illustrated, the stent 204 comprises a plurality of filaments 300. Each of the illustrated filaments 300 has been dipped in the coating material and an air stream has been applied to remove excess coating material from the filaments 300. The coating material thus remaining extends only along the filaments 300, without any webbing or delamination occurring.

In this embodiment, the filaments 300 cross each other in a generally orthogonal orientation relative to each other. As illustrated, the filaments 300 cross each other at angles of from about 75° to about 105°, or within from about 0° to about 15° from a right angle.

Generally, according to aspects of embodiments disclosed herein, when the filaments cross each other at substantially orthogonal or right angles (e.g., within about 15° from a right angle), the inter-filament space or crevice area (e.g., the gaps formed between surfaces of overlapping filaments at their crossing point) is minimized, thus reducing the space in which coating material can accumulate in excess of what is required to coat the filament surface. For example, an aspect of embodiments disclosed herein is the realization that the coating may be thicker in inter-filament spaces or crevices due to the surface tension of the coating material. Thus, reducing the inter-filament space can also reduce the amount of coating material captured therein by virtue of the coating material surface tension.

Figure 14A:
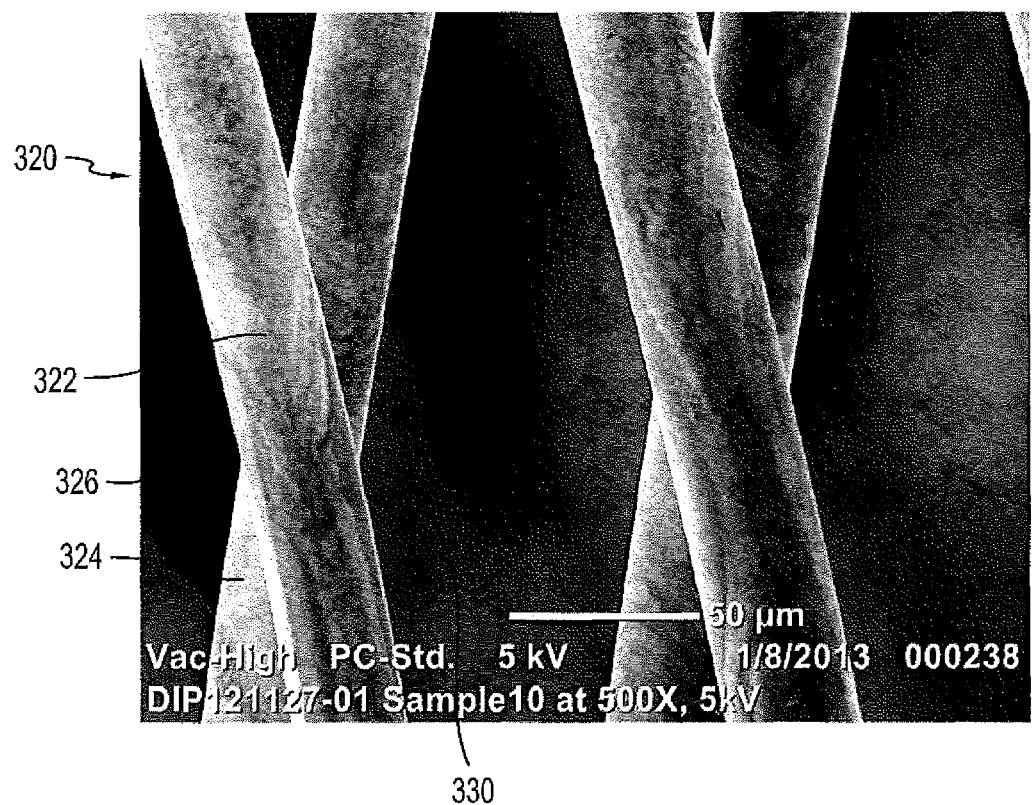
FIG. 14A is an enlarged view of a coated stent in a relaxed configuration, demonstrating no visible webbing or delamination, according to some embodiments.
Figure 14B:
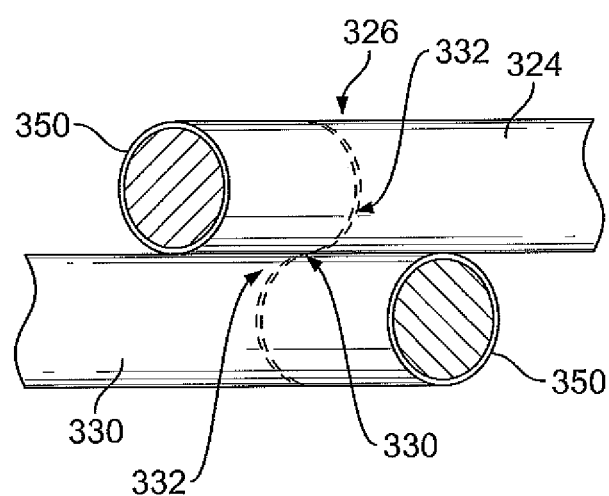
FIG. 14B is a detailed view of a filament crossing point of a coated stent.

For example, FIGS. 14A-B illustrate an embodiment of a stent 320 in which filaments 322, 324 overlap at a crossing point 326. FIG. 14A shows a coating that demonstrates excellent uniformity, smoothness, and is substantially free of webbing. The filaments 322, 324, which are generally cylindrical, generally have a single contact point 330. Due to the contact and overlap between the filaments 322, 324, an inter-filament or crevice area 332 is formed immediately adjacent to the single contact point 330. During the coating process, excess coating material can accumulate in the crevice areas 332, which can be difficult to remove. However, according to embodiments disclosed herein, the presence and size of inter-filament or crevice areas throughout the braided stent can be minimized by ensuring that the filaments of the portion of the stent to be coated are oriented substantially orthogonally relative to each other. Thus, in some embodiments, a thickness of a coating 350 disposed on the filaments 322, 324 can have a generally constant thickness, even along the crevice areas 332. Further, even with some coating material accumulation, the thickness of the coating 350 disposed in the crevice areas can be less than twice the thickness of the coating 350 disposed on the filaments 322, 324.

Some embodiments of the devices and methods disclosed herein can therefore provide a device, such as a stent or a braided stent, having a coating that is substantially free of webs, and in some embodiments, that also has a flow diverting pore size and/or a flow diverting porosity that is/are exhibited throughout the entire stent, or in a flow diverting portion or section of the stent. In one embodiment, a coated device, stent or section is "substantially free" of webs when any webs that are present are sufficiently few in number so as to not interfere with the function of the device. Alternatively, a coated device, stent or section that is substantially free of webs can be one in which there is webbing present at fewer than 5% of the filament crossing points, and/or at fewer than 5% of the pores. In another alternative, a coated device, stent or section that is substantially free of webs can be one in which there is webbing present at fewer than 3% of the filament crossing points, and/or at fewer than 3% of the pores. As yet another alternative, a coated device, stent or section can have no webbing at all in any of the filament crossing points, and/or in any of the pores.

Instead of or in addition to the substantial or complete absence of webbing discussed above, the coating of the device, stent or section can be substantially complete. Substantial completeness of coverage can be achieved when the filaments are covered completely along their length within the device, stent or section, with the exception of (a) uncoated areas amounting to less than 5%, or less than 3%, of the outer surface of the filaments, and/or (b) uncoated and/or less-coated (e.g. with fewer than all layers of a multi-layer coating) areas in some or all of the filament crossing points. Alternatively, the coated device, stent or section can be completely coated.

Instead of or in addition to the properties described above relating to lack of webs and/or completeness of coverage, the device, stent or section can be coated with an antithrombogenic coating sufficiently to reduce the thrombogenicity of the coated stent, device, section, etc. as compared to a similar but uncoated stent, device, section, etc. The reduction in thrombogenicity can be significant. Stents coated according to the method disclosed herein have been tested for increased antithrombogenicity via thrombogram, employing the following assay.

| Materials | | |
| --- | --- | --- |
| Description | Information/Purpose | Source |
| Human Platelet Packs | 240 mL stock of citrated aphorized human platelets in plasma (PRP) | Red Cross, Dedham, MA |
| Fluorogenic substrate | For thrombin detection (Z-Gly-Gly-Arg-AMC-HCl, 40 mM stock in dimethyl sulfoxide) | Bachem Americas, Inc., Torrance, CA Cat#: I-1140 |
| Calcium Chloride ($CaCl_2$) | For starting coagulation and thrombin generation (1M stock in Distilled Water) | Sigma Aldrich Corp., St. Louis, MO Cat#: 223506-2.5 KG |
| 4 mm Glass Spheres | Positive control for thrombin generation (assay only) | Fisher Scientific, Waltham, MA Cat# 11-312B |
| Sodium Hypochlorite | Storage of samples post-testing; Cleaning of glass spheres pre-testing | Clorox Co., Oakland, CA |
| Thrombin Calibrator | For calibration (RFU to Thrombin) autologous PPP | Diagnostica Stago, Inc., Parsippany, NJ Cat#: TS20.00, 1 mL vials |
| HEPES Buffered Saline | For preparation of and serial dilutions of Thrombin stock for calibration | Sigma Aldrich Cat#: 51558-50 ML |
| Dimethyl Sulfoxide | For substrate stock solution (25 mg/mL) | Sigma Aldrich Cat#: D8418-100 ML |
| 50 mL Reagent Reservoir Polystyrene | For loading sample solutions into Multipipette Dispenser | Fisher Scientific |

| Materials | | |
|---|---|---|
| Description | Information/Purpose | Source |
| Centrifuge | For obtaining platelet poor plasma (PPP) from PRP | Eppendorf North America, Hauppauge, NY 5810R |
| Rocker | For storing PRP bags until use | Fisher Scientific Labline |
| OptiPlate black/opaque 96-well microplate | For assaying fluorescence of multiple test samples and controls | Fisher Scientific |
| Synergy HT Plate Reader | For simultaneous kinetic fluorescence measurements of multiple samples | Biotek Instruments, Inc., Winooski, VT |
| Particle Counter | For platelet counts (final counts in plasma as required) | Beckman Coulter, Inc., Brea, CA |
| Multipipette Dispenser | For simultaneously dispensing reagents into multiple microplate wells | Mettler Toledo, Inc., Columbus, OH Rainin |
| Ruler/Calipers | Dimensions of test samples | MSC |
| Balance | For weighing of stent pieces | Mettler Toledo |

The citrated stock (~240 ml) of platelet rich plasma (PRP) was stored on the rocker (setting: 2) at room temperature for 3 days (up to a maximum of 1 day post printed expiration date). PPP (platelet poor plasma) was prepared on day 1 of obtaining the corresponding PRP stock, as follows: (a) pour 100 mL of PRP stock suspension into two 50 mL centrifuge tubes; (b) centrifuge for 30 minutes at 2900×g; (c) carefully pour out the supernatant-platelet poor plasma (PPP) and filter it using a 0.22 μm syringe-driven filter unit; (d) divide some of the PPP into 5 mL aliquots; (e) store the PPP aliquots at −80° C.; and (e) utilize 50 mL of PPP for dilution of autologous PRP for purposes of the assay.

Next, Diluted PRP was prepared as follows: (a) perform platelet count (counting particles within size range of 2 μm-4 μm for PRP stock solution) in the particle counter by priming the aperture and cleaning the apparatus with purified water, diluting 10 μL of PRP stock in 10 mL of electrolyte solution and initiating the count, and recording the mean platelet count of the PRP stock; (b) dilute PRP to a final count of 200,000 per μL with autologous PPP; and (c) calculate total volume of PRP and PPP needed for assay (per sample=250 μL).

Samples of stents that were coated according to the method disclosed herein ("test stents") and of identical but bare-metal stents ("bare stents") were prepared as follows: (a) cut sections of each stent to a length of 9 mm; (b) immerse the sections individually in a 1.5 mL centrifuge tube filled with deionized water for 30 minutes; and (c) after wetting, blot out the excess water from each stent section on a kimwipe.

The 96-well microplate was then loaded with the following: (a) test stent sections (5 wells); (b) bare stent sections (5 wells); (c) 4 mm glass spheres (5 wells, to function as a positive control); and (d) blanks (5 wells with no samples, serving as a negative control). Only one of a test stent section, bare stent section or glass sphere was placed in any one well. The plate reader was then turned on and allowed to warm up for three minutes, while the associated PC software (Gen 5) was launched. The settings used were: test temperature 25° C.; fluorescence reading (excitation (nm): 360/40, emission (nm): 460/40); no shake; kinetic reading every one minute for each well; total experimental time of two hours. Generally, the plate reader was set up for immediate read before preparing the test solutions.

Test solutions were prepared immediately before the analysis as follows. Experimental solution was prepared by adding fluorogenic substrate (25 mg/mL)(40 mM) to Diluted PRP (final count 200,000/μL) in a 15 mL centrifuge tube for a final concentration of 400 μM, then adding 1M calcium chloride for a final concentration of 20 mM, and inverting the tube to mix. Calibrator solutions were prepared by (a) adding 1 mL of deionized water to a 1 mL vial (as packaged) of the lyophilized thrombin calibrator; (b) preparing 10 mL of HBS-BSA solution (20 mM HEPES, 10 mg/ml bovine serum albumin (BSA), pH 7.4, filtered with the 0.22 μm syringe filter); (c) making four serial dilutions of the calibrator as prepared in step (a), in HBS-BSA (1:2, 1:20, 1:200, 1:2000); (d) adding 100 μL of the fluorogenic substrate to 10 mL of PPP; and (e) mixing five calibrator solutions as follows: (1) by mixing fourteen parts of the substrate-PPP mixture of step (d) with one part of the 1:2 dilution of step (c); (2) by mixing fourteen parts of the substrate-PPP mixture of step (d) with one part of the 1:20 dilution of step (c); (3) by mixing fourteen parts of the substrate-PPP mixture of step (d) with one part of the 1:200 dilution of step (c); (4) by mixing fourteen parts of the substrate-PPP mixture of step (d) with one part of the 1:2000 dilution of step (c); and (5) by mixing fourteen parts of the substrate-PPP mixture of step (d) with one part of the (undiluted) calibrator as prepared in step (a).

The test solutions were transferred to the microplate as follows: (a) 300 μL of the experimental solution in each of the wells containing a test stent section, a bare stent section, or a glass sphere, and in each of the five designated blanks; and (b) 300 μL of calibrator solution in each of ten wells containing no sample (separate from the blank wells), two wells each for each of the five calibrator solutions described above. A multipipette dispenser was used for the experimental solution to ensure that all wells were filled in less than one minute.

The microplate was then placed the reader and the test was run. The coated stents were found to result in a significant delay in peak thrombin formation, as compared to a similar but uncoated stent. In particular, the elapsed time before peak thrombin formation was found to be about 2.5 times that of the similar but uncoated stent. In another experimental run, the elapsed time before peak thrombin formation was found to be about 1.5 times that of the similar but uncoated stent. Accordingly, the time before peak thrombin formation with the coated device, stent, section, etc. can be more than 1.5 times, or more than twice, or about 2.5 times, or about 1.5 times that of a similar but uncoated device, stent, section, etc.

Figure 17A:
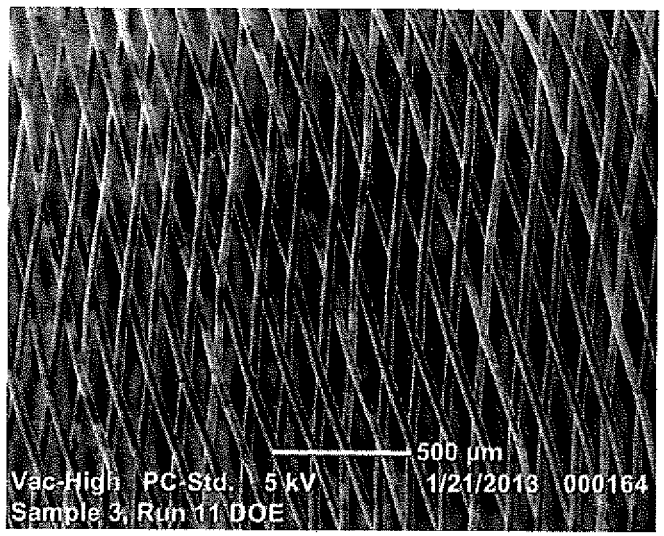
FIGS. 17A-17C are views of another stent coated according to some embodiments, demonstrating no webbing or delamination of the coating.
Figure 17B:
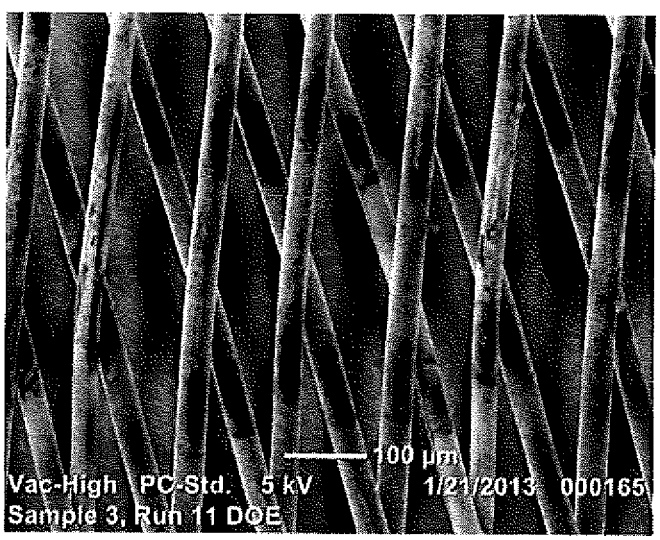
Figure 17C:
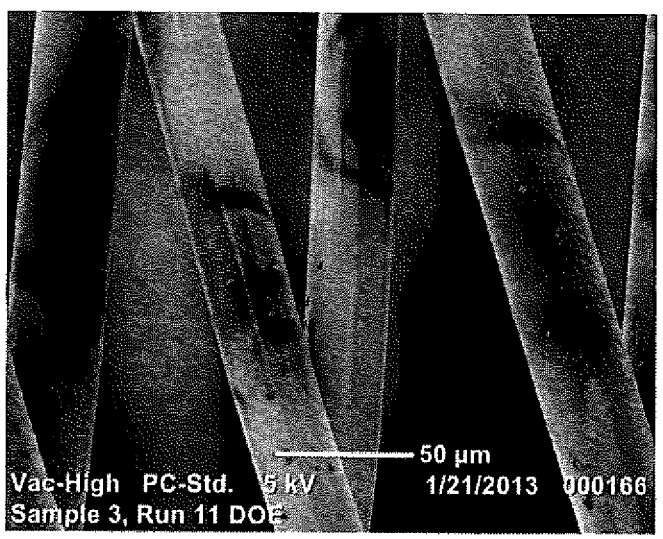
Figure 18A:
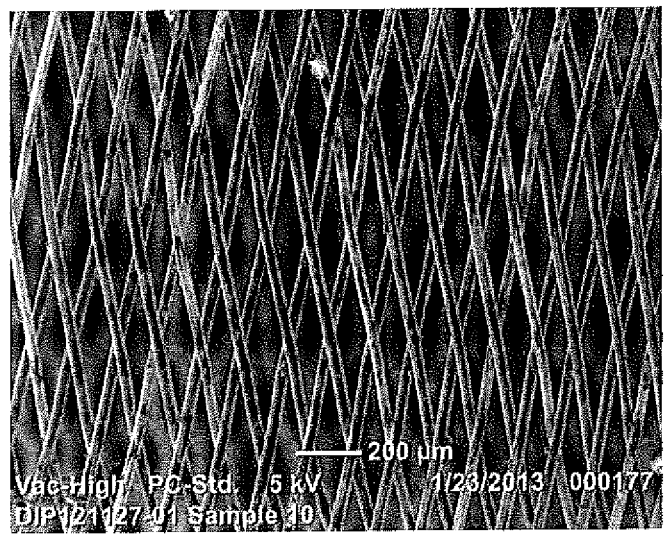
FIGS. 18A-18C are views of yet another stent coated according to some embodiments, demonstrating no webbing or delamination of the coating.
Figure 18B:
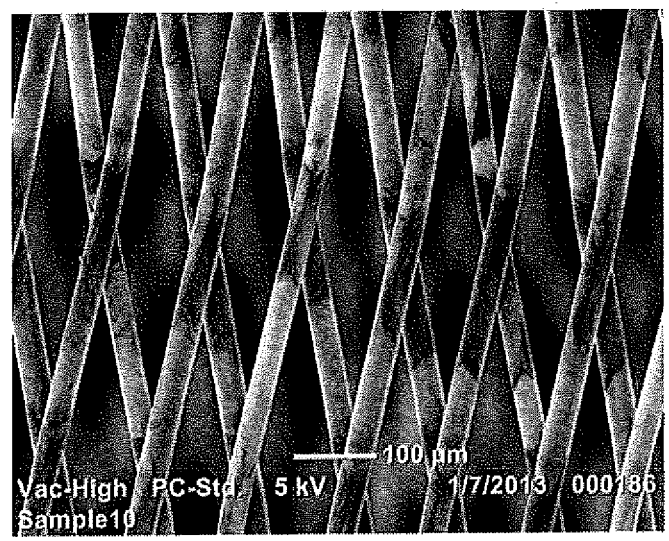
Figure 18C:
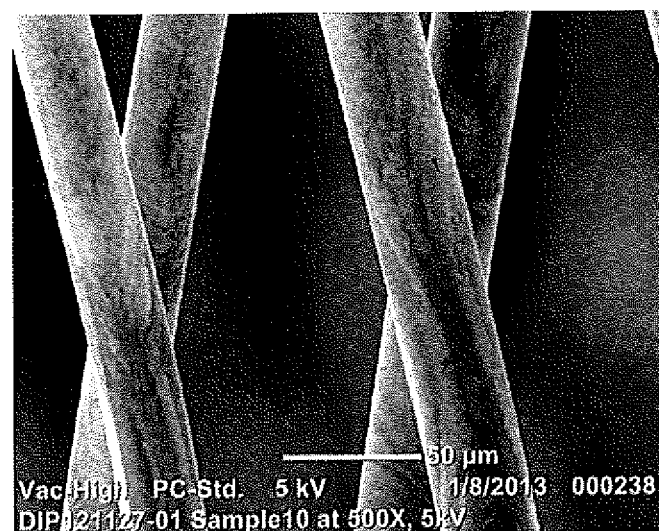
Figure 19A:
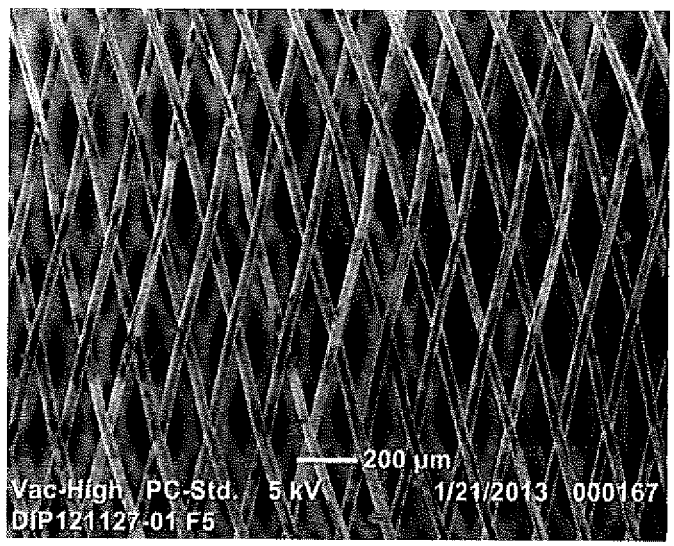
FIGS. 19A-19C are views of yet another stent coated according to some embodiments, demonstrating no webbing or delamination of the coating.
Figure 19B:
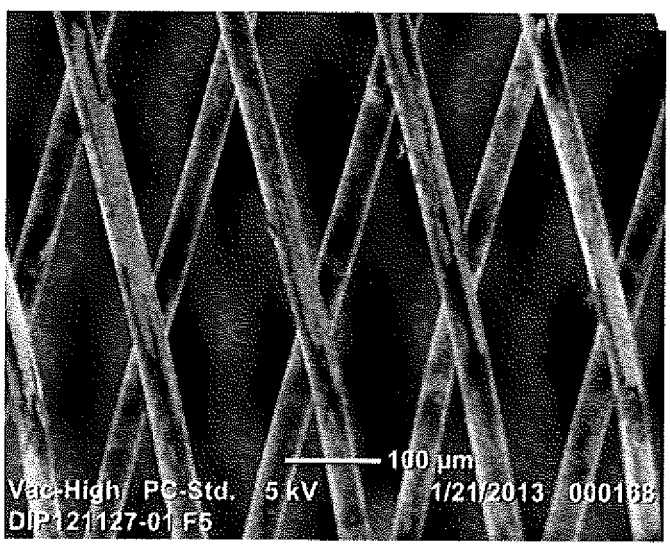
Figure 19C:
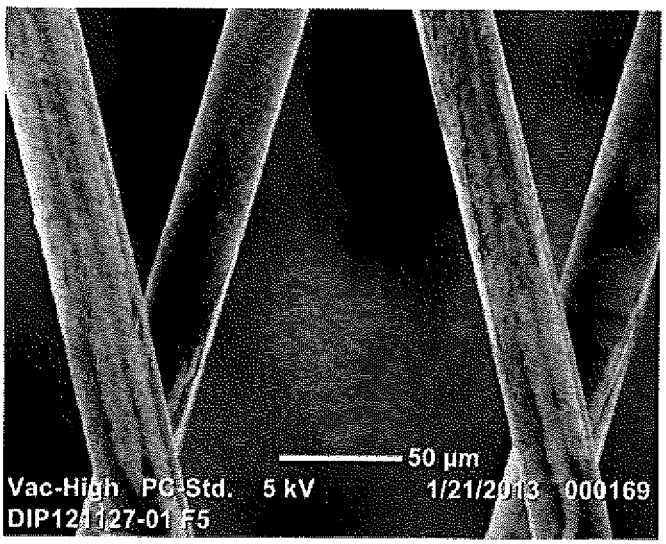

The substantial or complete absence of webbing in the coated device, stent, section, etc. can be observed in SEM (scanning electron microscope) imaging. FIGS. 16A-19C are SEM images of four different braided stents that were coated using the process disclosed herein and according to the parameters shown in Table 1, each at three levels of magnification: 50× (the "A" images), 150× (the "B" images), and 500× (the "C" images). No webbing can be observed in any of these images. From observation of the images, the pore size of the stent shown in FIGS. 16C and 19C, as measured by the diameter of an inscribed circle within the pore, is approximately 110 microns. The pore size of the pores illustrated in FIGS. 17C and 18C is approximately 80 microns.

Figure 15:
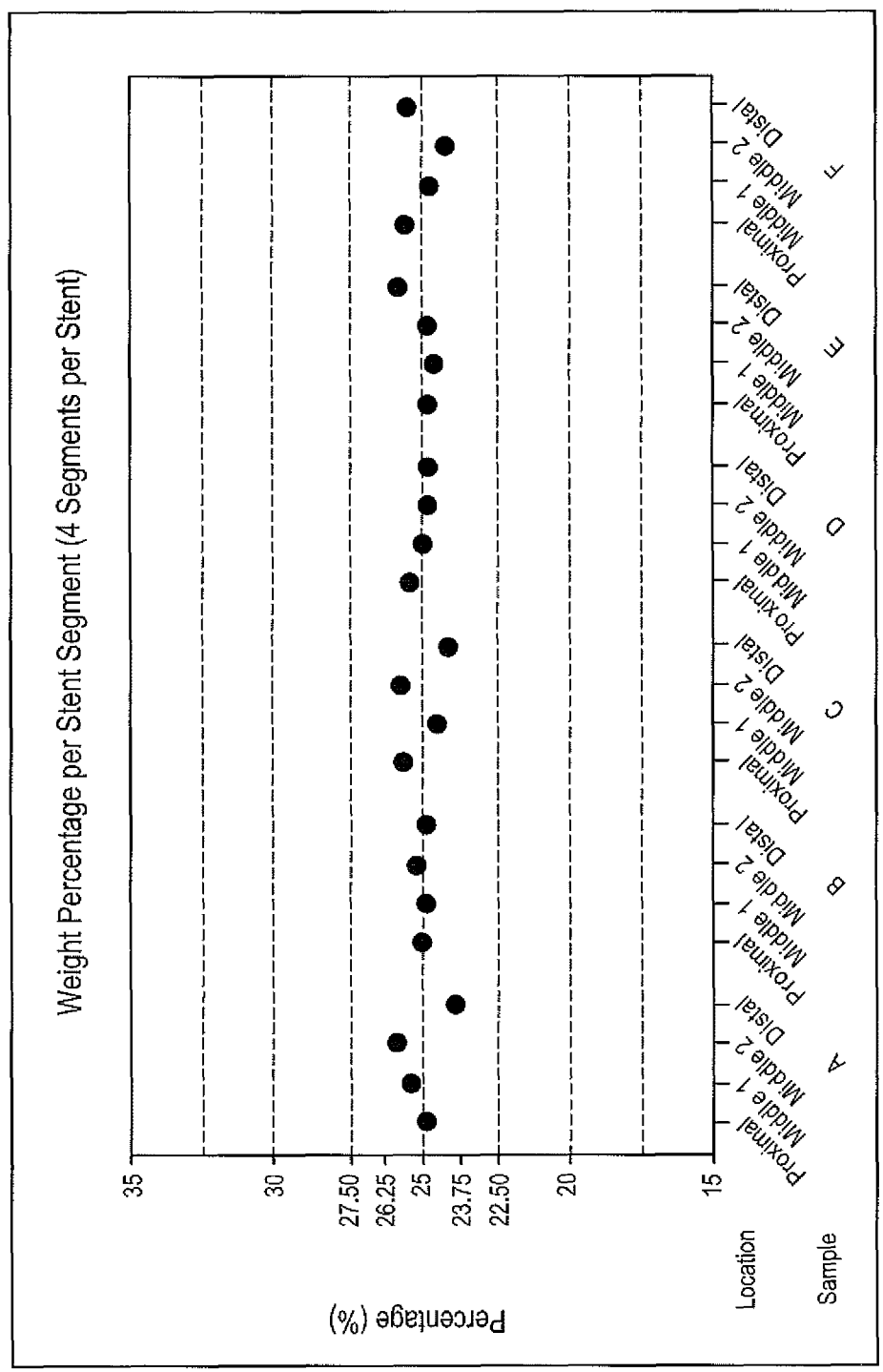
FIG. 15 is a chart of weight gain measured in series of longitudinal sections of six coated stents.
Figure 16A:
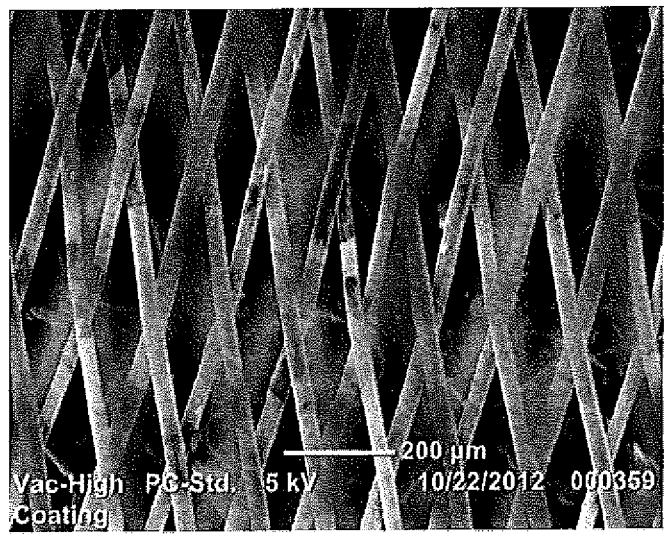
FIGS. 16A-16C are views of a stent coated according to some embodiments, demonstrating no webbing or delamination of the coating.
Figure 16B:
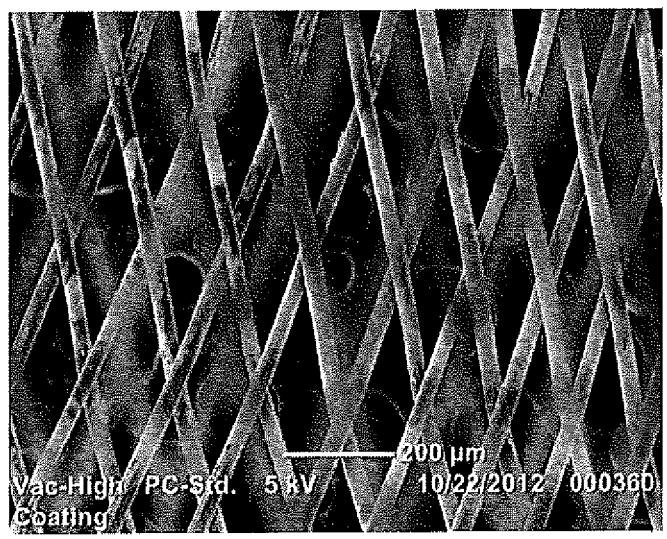
Figure 16C:
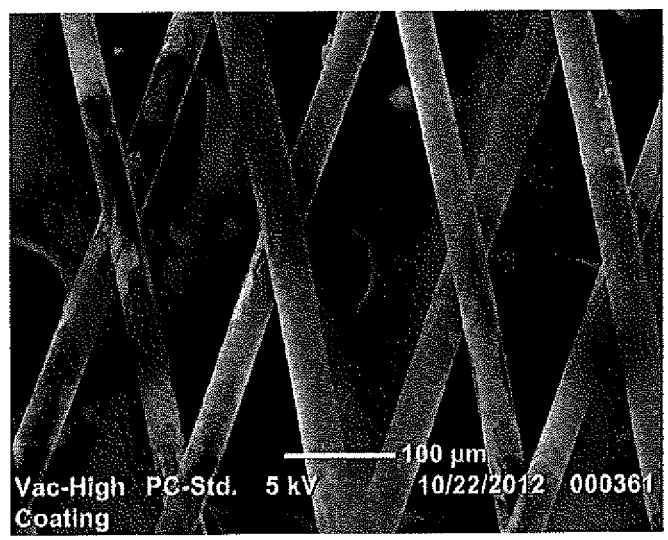

FIGS. 16A-19C also show complete coverage of the coated stents. Completeness or substantial completeness of coverage, as well as coating uniformity, can also be observed from weight-gain data obtained from coated stents. FIG. 15 depicts the results of a weight-gain study performed on six stents that were coated with the process disclosed herein and according to the parameters shown in Table 1. After coating, each stent was cut into four equal-length longitudinal sections (Proximal, Middle #1, Middle #2 and Distal) that were weighed separately to compute a percent weight gain for each stent section. (The bare weight of each section was determined as ¼ of the pre-coating weight of the stent.) As can be seen in FIG. 15, the percent weight gain was highly consistent across all the 24 stent sections. These data indicate completeness or substantial completeness of coverage, as well as uniformity of coverage, because a process that generates piecemeal or gap-laden coverage would be expected to result in high variance in weight gain among the measured sections.

Accordingly, instead of or in addition to the other coating properties discussed herein, the device, stent or section can have a coating weight gain in each of four longitudinal sections of the device, stent or section, wherein the weight gain varies by no more than 2.5 percentage points, or no more than 4 percentage points, or no more than 5 percentage points, between the largest and smallest gains among the four sections.

Example 1

Braided tubular stents were coated according to the process described herein and the parameters provided in Table 1. Each of the stents was configured as follows: 48 braided filaments, of which 12 were of platinum alloyed with 8% tungsten, with 0.0012 inch filament diameter, 12 were of 35 NLT, with 0.0012 inch filament diameter, and 24 were of 35 NLT, with 0.0014 inch filament diameter; overall outside diameter 5.2 mm and longitudinal picks per inch of 275, both dimensions prevailing when in an expanded, unconstrained and unstretched condition.

The stents were provided in their "bare metal" condition, and prepared as follows. First, they were washed in 99.5% acetone for five minutes in an ultrasonic cleaner, and then washed in 99% isopropyl alcohol (IPA) in an ultrasonic cleaner, in two separate five-minute IPA wash stages. After washing, the stents were rinsed in distilled water and then dried in an oven at 60 degrees C. for 30 minutes.

A coating solution of 2-Methacryloyloxyethyl phosphorylcholine (MPC) was prepared by dissolving 2.0 grams of MPC (LIPIDURE™-CM2056) in 200 milliliters of ethanol, and provided in a beaker at room temperature. The coating process was then performed on each of the stents, according to the description provided herein and the parameters shown in Table 1. After completion of the process and trimming, the stents could be described as tubular braided stents, open at each end with a lumen extending from one end to the other, and with a coating of MPC over the entirety of the stent filaments.

FIGS. 16A-19C are SEM images of four stents coated according to this Example 1. As described previously, the images indicate that the stents are coated completely and with no observable webbing in the pores.

FIG. 15 depicts the results of a weight gain study performed on six stents coated according to this Example 1. Again, the weight-gain data shows that the stents were coated completely or substantially completely, and with high uniformity.

Stents coated according to this Example 1 were tested for increased antithrombogenicity via thrombogram, employing the assay described above. The coated stents were found to result in a significant delay in peak thrombin formation, as compared to an identical but uncoated stent. In particular, the elapsed time before peak thrombin formation was found to be about 2.5 times the time observed with the identical but uncoated stent.

Methods of Treatment

As mentioned elsewhere herein, the present disclosure also includes methods of treating a vascular condition, such as an aneurysm or intracranial aneurysm, with any of the embodiments of the coated stents disclosed herein. The coated, low-thrombogenicity stent could be deployed across the neck of an aneurysm and its flow-diverting properties employed to reduce blood flow between the aneurysm and the parent vessel, cause the blood inside the aneurysm to thrombose and lead to healing of the aneurysm.

Significantly, the low-thrombogenicity stents disclosed herein can facilitate treatment of a large population of patients for whom flow-diverter therapy has not been previously possible. Such patients are those who have previously suffered from a hemorrhagic aneurysm or who have been diagnosed as being at risk for hemorrhage from an aneurysm or other vascular anatomy such as from the intracranial arterial system. These patients cannot currently be treated with commercially available flow-diverting stents because those stents are bare metal, braided stents whose implantation requires the patient to take blood-thinning medication (typically aspirin and PLAVIX™ (clopidogrel)) for a long period of time following implantation. The purpose of the blood-thinning medication is to counteract the tendency of the bare-metal stent to cause thrombus (blood clots) to form in the patient's vasculature. However, for a patient who has suffered or is at risk of intracranial hemorrhage, taking the blood-thinning medication can cause, or put the patient at higher risk of, such a hemorrhage. Low-thrombogenicity flow-diverting stents, such as the coated stents disclosed herein, can make flow-diverter therapy possible for patients who cannot tolerate blood-thinning medication because the reduced thrombogenicity can reduce or eliminate the need for blood thinners.

In order to implant any of the coated stents disclosed herein, the stent can be mounted in a delivery system. Suitable delivery systems are disclosed in U.S. patent application Ser. No. 13/692,021, filed Dec. 3, 2012, titled METHODS AND APPARATUS FOR LUMINAL STENTING;

and in U.S. Pat. No. 8,273,101, issued Sep. 25, 2012, titled SYSTEM AND METHOD FOR DELIVERING AND DEPLOYING AN OCCLUDING DEVICE WITHIN A VESSEL. The entire contents of both of these documents are incorporated by reference herein and made a part of this specification. In particular, these documents' teachings regarding braided stent delivery systems and methods may be employed to deliver any of the coated stents disclosed herein in the same manner, to the same bodily location(s), and using the same components as are disclosed in both incorporated documents.

Generally, as shown in FIG. 20, a delivery system 400 may be used to deliver a stent 402 into a hollow anatomical structure, such as a blood vessel. The delivery system 400 can include an elongate core assembly 404 that supports or contains the stent 402, and both components can be slidably received in a lumen 410 of a microcatheter 412 or other elongate sheath for delivery to any region to which the distal opening of the microcatheter 412 can be advanced. The core assembly 404 is employed to advance the stent 402 through the microcatheter 412 and out the distal end of the microcatheter 412 so that the stent 402 is allowed to self-expand into place in the blood vessel, across an aneurysm or other treatment location. The core assembly 404 can comprise a wire (e.g. a guidewire), a tube (e.g. a hypotube such as a spiral-cut or slotted hypotube), or a combination of a wire and a tube. The delivery system 400 may employ a polymeric member 420 that engages an inner wall of the tubular body and enables longitudinal force transmission from the core assembly 404 to the tubular body. Such a polymeric member can be mounted on the wire and/or tube.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery. The microcatheter is then advanced over the guidewire to the treatment location and situated so that a distal open end of the guidewire is adjacent to the treatment location. The guidewire can then be withdrawn from the microcatheter and the core assembly, together with the stent mounted thereon or supported thereby, can be advanced through the microcatheter and out the distal end thereof. The stent can then self-expand into apposition with the inner wall of the blood vessel. Where an aneurysm is being treated, the stent is placed across the neck of the aneurysm so that a sidewall of the stent (e.g. a section of the braided tube) separates the interior of the aneurysm from the lumen of the parent artery. Once the stent has been placed, the core assembly and microcatheter are removed from the patient. The stent sidewall can now perform a flow-diverting function on the aneurysm, thrombosing the blood in the aneurysm and leading to healing of the aneurysm.

Because of the low-thrombogenic properties of the coated stents disclosed herein, certain additional aspects of the methods of treatment are possible. For example, the patient can be one who has previously suffered from, or who has been diagnosed as being at risk, of hemorrhage from an aneurysm or other arterial anatomy such as the intracranial arterial system. The patient can be prescribed a reduced regimen of blood-thinning medication as compared to the regimen that would be necessary for patient who received an otherwise similar but uncoated flow-diverting stent. The regimen can be "reduced" in the sense that the patient takes a lower dosage, fewer medications, less powerful medications, follows a lower dosage frequency, and/or takes medication for a shorter period of time following implantation of the stent, or otherwise. Alternatively, the patient may be prescribed no blood thinning medication at all.

The devices and methods discussed herein are not limited to the coating of stents, but may include any number of other implantable devices. Treatment sites may include blood vessels and areas or regions of the body such as organ bodies.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A medical device for treating an aneurysm, comprising:
   a tubular member comprising a plurality of braided filaments that form a sidewall and a plurality of pores in the sidewall that are sized to inhibit flow of blood through the sidewall into an aneurysm to a degree sufficient to lead to thrombosis and healing of the aneurysm when the tubular member is positioned in a blood vessel and adjacent to the aneurysm, each of the filaments crossing another of the filaments at a respective crossing point; and
   an antithrombogenic material distributed over the tubular member such that the pores are substantially free of webs formed by the material such that webs are present at fewer than 5% of the crossing points;
   wherein the tubular member exhibits a weight gain in each of four longitudinal sections of the tubular member compared to an identical, uncoated tubular member, and
   wherein the weight gain varies by no more than 5 percentage points between the largest and smallest gains among the four longitudinal sections.

2. The medical device of claim 1, wherein the weight gain varies by no more than 2.5 percentage points between the largest and the smallest gains among the four sections.

3. The medical device of claim 1, wherein the pores have an average pore size that is less than or equal to about 500 microns when the member is in an expanded state.

4. The medical device of claim 1, wherein the pores have an average pore size that is less than or equal to about 320 microns when the member is in an expanded state.

5. The medical device of claim 3, wherein the pores have an average pore size that is measured using an inscribed circle diameter.

6. The medical device of claim 1, wherein the tubular member has a porosity that is greater than or equal to about 50% and less than or equal to about 85% when the member is in an expanded state.

7. The medical device of claim 1, wherein the distribution of the antithrombogenic material is substantially complete over the tubular member.

8. The medical device of claim 1, wherein the distribution of the antithrombogenic material is substantially complete over at least a circumferential section of the tubular member that is 5 mm or more in length.

9. The medical device of claim 8, wherein the antithrombogenic material comprises an anti-thrombogenic polymer.

10. The medical device of claim 9, wherein the antithrombogenic polymer comprises 2-Methacryloyloxyethyl phosphorylcholine.

11. A medical device for treating an aneurysm, comprising:
a tubular body configured to be implanted in a blood vessel and comprising a plurality of braided filaments, the body being expandable to an expanded state for treatment of the aneurysm, the body having a first section for spanning the neck of the aneurysm and a plurality of pores located between the filaments, each of the filaments crossing another of the filaments at a respective crossing point; and
the first section having a substantially complete distribution of antithrombogenic material over the filaments;
wherein the first section is substantially free of webs formed by the antithrombogenic material such that webs are present at fewer than 5% of the crossing points,
wherein the first section of the tubular body exhibits a weight gain in each of four longitudinal sections of the first section of the tubular body compared to an identical, uncoated tubular body, and
wherein the weight gain varies by no more than 5 percentage points between the largest and smallest gains among the four longitudinal sections.

12. The medical device of claim 11, wherein the weight gain varies by no more than 2.5 percentage points between the largest and the smallest gains among the four longitudinal sections.

13. The medical device of claim 11, wherein the pores have an average pore size that is less than or equal to about 500 microns when the body is in the expanded state.

14. The medical device of claim 11, wherein the pores have an average pore size that is less than or equal to about 320 microns when the body is in the expanded state.

15. The medical device of claim 13, wherein the pores have an average pore size that is measured using an inscribed circle diameter.

16. The medical device of claim 11, wherein the first section has a porosity that is greater than or equal to about 50% and less than or equal to about 85% when the body is in the expanded state.

17. The medical device of claim 11, wherein the first section comprises less than an entire length of the tube.

18. The medical device of claim 11, wherein the distribution of the antithrombogenic material is substantially complete over at least a circumferential section of the first section that is 5 mm or more in length.

19. The medical device of claim 18, wherein the antithrombogenic material comprises an anti-thrombogenic polymer.

20. The medical device of claim 19, wherein the antithrombogenic polymer comprises 2-Methacryloyloxyethyl phosphorylcholine.

* * * * *